(12) United States Patent
Zaidat et al.

(10) Patent No.: US 11,986,189 B2
(45) Date of Patent: May 21, 2024

(54) SYSTEMS AND METHODS FOR TREATING ANEURYSMS

(71) Applicant: Galaxy Therapeutics, Inc., Milpitas, CA (US)

(72) Inventors: Osama O. Zaidat, Lambertville, MI (US); Tiffany Tran Ngo, San Jose, CA (US); Razmik Soltanian, San Jose, CA (US); Edgard Luiz Ramos Pereira, Boca Raton, FL (US); Arturo Rosqueta, San Jose, CA (US); Thomas J. Wolfe, Shorewood, WI (US); Aamir Badruddin, Bolingbrook, IL (US)

(73) Assignee: Galaxy Therapeutics, Inc., Milpitas, CA (US)

( * ) Notice: Subject to any disclaimer, the term of this patent is extended or adjusted under 35 U.S.C. 154(b) by 0 days.

(21) Appl. No.: 18/353,880

(22) Filed: Jul. 17, 2023

(65) Prior Publication Data
US 2023/0355243 A1 Nov. 9, 2023

Related U.S. Application Data

(63) Continuation of application No. PCT/US2022/013986, filed on Jan. 27, 2022.
(Continued)

(51) Int. Cl.
*A61B 17/12* (2006.01)

(52) U.S. Cl.
CPC .. *A61B 17/12172* (2013.01); *A61B 17/12113* (2013.01); *A61B 17/12177* (2013.01); *A61B 2017/1205* (2013.01)

(58) Field of Classification Search
CPC ........ A61B 17/12172; A61B 17/12113; A61B 17/12177; A61B 2017/1205
See application file for complete search history.

(56) References Cited

U.S. PATENT DOCUMENTS

| 5,250,071 A | 10/1993 | Palermo |
| 5,282,806 A | 2/1994 | Haber et al. |

(Continued)

FOREIGN PATENT DOCUMENTS

| CN | 102871700 B | 4/2015 |
| CN | 103006285 B | 6/2015 |

(Continued)

OTHER PUBLICATIONS

Shapiro, M., Raz, E., Becske, T., Nelson, P., "Variable Porosity of the Pipeline Embolization Device in Straight and Curved Vessels: A Guide for Optimal Deployment Strategy", Original Research Interventional, Sep. 26, 2013, 6 pages, 10.3174/ajnr.A3742, American Society of Neuroradiology, Oak Brook, USA.

(Continued)

*Primary Examiner* — Sarah A Long
*Assistant Examiner* — Raihan R Khandker
(74) *Attorney, Agent, or Firm* — BLAIR WALKER IP SERVICES, LLC

(57) ABSTRACT

An apparatus for treating an aneurysm in a blood vessel includes an occlusion element configured to be releasably coupled to an elongate delivery shaft and configured to be delivered in a collapsed configuration through an inner lumen of a delivery catheter, the occlusion element including an inverted mesh tube having an outer layer and an inner layer, the outer layer transitioning to the inner layer at an inversion fold, wherein at least the outer layer is formed into a first expanded shape including: a smooth outer cylinder configured to engage a wall of an aneurysm throughout a 360° circumference; and a substantially distal-facing surface including one or more heat-formed undulations, the one or more undulations configured to apply a radial force on the wall of the aneurysm.

20 Claims, 29 Drawing Sheets

Related U.S. Application Data

(60) Provisional application No. 63/213,030, filed on Jun. 21, 2021, provisional application No. 63/142,480, filed on Jan. 27, 2021.

(56) References Cited

U.S. PATENT DOCUMENTS

| | | | |
|---|---|---|---|
| 5,304,195 | A | 4/1994 | Twyford, Jr. et al. |
| 5,556,390 | A | 9/1996 | Hicks |
| 5,795,331 | A | 8/1998 | Cragg et al. |
| 5,935,148 | A | 8/1999 | Villar et al. |
| 6,086,577 | A | 7/2000 | Ken et al. |
| 6,093,199 | A | 7/2000 | Brown et al. |
| 6,152,144 | A | 11/2000 | Lesh et al. |
| 6,391,037 | B1 | 5/2002 | Greenhalgh |
| 6,454,780 | B1 | 9/2002 | Wallace |
| 6,506,204 | B2 | 1/2003 | Mazzochi |
| 6,544,163 | B2 | 4/2003 | Wallace et al. |
| 6,613,074 | B1 | 9/2003 | Mitelberg et al. |
| D493,223 | S | 7/2004 | Solymar |
| 6,936,055 | B1 | 8/2005 | Ken et al. |
| 6,994,689 | B1 | 2/2006 | Zadno-Azizi et al. |
| 7,128,736 | B1 | 10/2006 | Abrams et al. |
| 7,195,636 | B2 | 3/2007 | Avellanet et al. |
| 7,229,461 | B2 | 6/2007 | Chin et al. |
| 7,367,985 | B2 | 5/2008 | Mazzochi et al. |
| 7,410,482 | B2 | 8/2008 | Murphy et al. |
| 7,569,066 | B2 | 8/2009 | Gerberding et al. |
| 7,749,242 | B2 | 7/2010 | Tran et al. |
| 8,142,456 | B2 | 3/2012 | Rosqueta et al. |
| 8,333,796 | B2 | 12/2012 | Tompkins et al. |
| 8,388,650 | B2 | 3/2013 | Gerberding et al. |
| 8,398,670 | B2 | 3/2013 | Amplatz et al. |
| 8,551,132 | B2 | 10/2013 | Eskridge et al. |
| 8,597,320 | B2 | 12/2013 | Sepetka et al. |
| 8,728,117 | B1 | 5/2014 | Janardhan et al. |
| 8,777,979 | B2 | 7/2014 | Shrivastava et al. |
| D713,527 | S | 9/2014 | Heipl |
| 8,820,207 | B2 | 9/2014 | Marchand et al. |
| 8,826,791 | B2 | 9/2014 | Thompson et al. |
| 8,864,790 | B2 | 10/2014 | Strauss et al. |
| 8,864,791 | B2 | 10/2014 | Bloom et al. |
| 8,940,015 | B2 | 1/2015 | Kariniemi |
| D727,500 | S | 4/2015 | Heipl |
| D727,501 | S | 4/2015 | Heipl |
| D728,102 | S | 4/2015 | Heipl |
| 8,998,947 | B2 | 4/2015 | Aboytes et al. |
| 9,107,670 | B2 | 8/2015 | Hannes et al. |
| 9,113,890 | B2 | 8/2015 | Dasnukar et al. |
| 9,179,899 | B2 | 11/2015 | Freudenthal |
| 9,198,668 | B2 | 12/2015 | Theobald et al. |
| 9,259,337 | B2 | 2/2016 | Cox et al. |
| 9,314,326 | B2 | 4/2016 | Wallace et al. |
| 9,510,811 | B2 | 12/2016 | Akpinar |
| 9,585,670 | B2 | 3/2017 | Hines |
| 9,597,087 | B2 | 3/2017 | Marchand et al. |
| 9,636,117 | B2 | 5/2017 | Bachman et al. |
| 9,669,188 | B2 | 6/2017 | Echarri et al. |
| 9,855,052 | B2 | 1/2018 | Aboytes et al. |
| 9,877,726 | B2 | 1/2018 | Liu et al. |
| 9,918,720 | B2 | 3/2018 | Marchand et al. |
| 9,980,733 | B2 | 5/2018 | Badruddin et al. |
| 10,111,670 | B2 | 10/2018 | Lorenzo et al. |
| 10,123,805 | B2 | 11/2018 | Ayres et al. |
| 10,136,896 | B2 | 11/2018 | Hewitt et al. |
| 10,149,676 | B2 | 12/2018 | Mirigian et al. |
| 10,478,195 | B2 | 11/2019 | Aboytes et al. |
| 10,751,065 | B2 | 8/2020 | Soto del Valle et al. |
| 10,792,045 | B2 | 10/2020 | Wang et al. |
| 10,856,880 | B1 | 12/2020 | Badruddin et al. |
| 11,026,694 | B2 | 6/2021 | Wang et al. |
| 11,058,431 | B2 | 7/2021 | Pereira et al. |
| 11,166,731 | B2 | 11/2021 | Wolfe et al. |
| 11,202,636 | B2 | 12/2021 | Zaidat et al. |
| 11,278,292 | B2 | 3/2022 | Gorochow et al. |
| 11,413,046 | B2 | 8/2022 | Xu et al. |
| 11,497,504 | B2 | 11/2022 | Xu et al. |
| 11,559,309 | B2 | 1/2023 | Rangwala et al. |
| 11,583,282 | B2 | 2/2023 | Gorochow et al. |
| 11,596,412 | B2 | 3/2023 | Xu et al. |
| 11,602,350 | B2 | 3/2023 | Gorochow et al. |
| 2002/0169473 | A1 | 11/2002 | Sepetka et al. |
| 2002/0188314 | A1 | 12/2002 | Anderson et al. |
| 2003/0171770 | A1 | 9/2003 | Kusleika et al. |
| 2003/0176884 | A1 | 9/2003 | Berrada et al. |
| 2003/0195553 | A1 | 10/2003 | Wallace et al. |
| 2004/0034386 | A1 | 2/2004 | Fulton et al. |
| 2004/0044391 | A1 | 3/2004 | Porter |
| 2004/0172056 | A1 | 9/2004 | Guterman et al. |
| 2004/0199201 | A1 | 10/2004 | Kellett et al. |
| 2005/0033409 | A1 | 2/2005 | Burke et al. |
| 2005/0107823 | A1 | 5/2005 | Leone et al. |
| 2005/0171478 | A1 | 8/2005 | Selmon et al. |
| 2005/0277978 | A1 | 12/2005 | Greenhalgh |
| 2006/0064151 | A1 | 3/2006 | Guterman et al. |
| 2006/0106417 | A1 | 5/2006 | Tessmer et al. |
| 2006/0155323 | A1 | 7/2006 | Porter et al. |
| 2007/0173928 | A1 | 7/2007 | Morsi |
| 2007/0208376 | A1 | 9/2007 | Meng |
| 2007/0225794 | A1 | 9/2007 | Thramann et al. |
| 2007/0270902 | A1 | 11/2007 | Slazas et al. |
| 2008/0045997 | A1 | 2/2008 | Balgobin et al. |
| 2008/0097495 | A1 | 4/2008 | Feller, III et al. |
| 2008/0147100 | A1 | 6/2008 | Wallace |
| 2008/0281350 | A1 | 11/2008 | Sepetka et al. |
| 2008/0319533 | A1 | 12/2008 | Lehe |
| 2009/0062841 | A1 | 3/2009 | Amplatz et al. |
| 2009/0082803 | A1 | 3/2009 | Adams et al. |
| 2009/0099647 | A1 | 4/2009 | Glimsdale et al. |
| 2009/0177261 | A1 | 7/2009 | Teoh et al. |
| 2009/0264978 | A1 | 10/2009 | Dieck et al. |
| 2009/0287291 | A1 | 11/2009 | Becking et al. |
| 2009/0318941 | A1 | 12/2009 | Sepetka et al. |
| 2010/0179583 | A1 | 7/2010 | Carpenter et al. |
| 2011/0046719 | A1 | 2/2011 | Frid |
| 2011/0144669 | A1 | 6/2011 | Becking et al. |
| 2011/0152993 | A1 | 6/2011 | Marchand et al. |
| 2011/0202085 | A1 | 8/2011 | Loganathan et al. |
| 2012/0065667 | A1 | 3/2012 | Javois et al. |
| 2012/0071911 | A1 | 3/2012 | Sadasivan et al. |
| 2012/0143317 | A1 | 6/2012 | Cam et al. |
| 2012/0245675 | A1 | 9/2012 | Molaei et al. |
| 2012/0259244 | A1 | 10/2012 | Roberts et al. |
| 2012/0283768 | A1 | 11/2012 | Cox et al. |
| 2012/0303052 | A1 | 11/2012 | Connor |
| 2012/0310270 | A1 | 12/2012 | Murphy et al. |
| 2012/0330347 | A1 | 12/2012 | Becking et al. |
| 2013/0066357 | A1 | 3/2013 | Abotes et al. |
| 2013/0073026 | A1 | 3/2013 | Russo et al. |
| 2013/0190800 | A1 | 7/2013 | Murphy et al. |
| 2013/0211495 | A1 | 8/2013 | Halden et al. |
| 2014/0005714 | A1 | 1/2014 | Quick et al. |
| 2014/0012303 | A1 | 1/2014 | Heipl |
| 2014/0052233 | A1 | 2/2014 | Cox et al. |
| 2014/0172001 | A1 | 6/2014 | Becking et al. |
| 2014/0257360 | A1 | 9/2014 | Keillor |
| 2014/0277013 | A1 | 9/2014 | Sepetka et al. |
| 2014/0343602 | A1 | 11/2014 | Cox et al. |
| 2015/0005810 | A1* | 1/2015 | Center ............... A61B 17/0057 606/200 |
| 2015/0005811 | A1 | 1/2015 | Lubock et al. |
| 2015/0133989 | A1 | 5/2015 | Lubock et al. |
| 2015/0250628 | A1 | 9/2015 | Monstadt et al. |
| 2015/0272589 | A1 | 10/2015 | Lorenzo |
| 2015/0313605 | A1 | 11/2015 | Griffin |
| 2016/0022445 | A1 | 1/2016 | Ruvalcava et al. |
| 2016/0030050 | A1 | 2/2016 | Franano et al. |
| 2016/0278749 | A1 | 9/2016 | Javois et al. |
| 2016/0317277 | A1 | 11/2016 | Carpenter et al. |
| 2017/0014114 | A1 | 1/2017 | Radfiee et al. |
| 2017/0156734 | A1 | 6/2017 | Griffin |
| 2017/0224350 | A1 | 8/2017 | Shimizu et al. |
| 2017/0224355 | A1* | 8/2017 | Bowman ............... D04C 1/06 |
| 2017/0348014 | A1 | 12/2017 | Wallace et al. |

(56) References Cited

U.S. PATENT DOCUMENTS

| | | |
|---|---|---|
| 2017/0367708 A1 | 12/2017 | Mayer et al. |
| 2017/0367713 A1 | 12/2017 | Greene, Jr. et al. |
| 2018/0049731 A1 | 2/2018 | Hardy et al. |
| 2018/0242979 A1 | 8/2018 | Lorenzo |
| 2019/0053810 A1 | 2/2019 | Griffin |
| 2019/0110796 A1 | 4/2019 | Jayaraman |
| 2019/0192165 A1 | 6/2019 | Greene, Jr. et al. |
| 2019/0192167 A1 | 6/2019 | Lorenzo |
| 2019/0192168 A1 | 6/2019 | Lorenzo |
| 2019/0223876 A1 | 7/2019 | Badruddin et al. |
| 2019/0223878 A1 | 7/2019 | Lorenzo et al. |
| 2019/0223881 A1 | 7/2019 | Hewitt et al. |
| 2019/0357914 A1 | 11/2019 | Gorochow et al. |
| 2020/0113576 A1 | 4/2020 | Gorochow et al. |
| 2020/0367900 A1 | 11/2020 | Pedroso et al. |
| 2020/0367906 A1 | 11/2020 | Xu et al. |
| 2021/0085333 A1* | 3/2021 | Gorochow ....... A61B 17/12031 |
| 2021/0128160 A1 | 5/2021 | Li et al. |
| 2021/0128161 A1 | 5/2021 | Nageswaran et al. |
| 2021/0128162 A1 | 5/2021 | Rhee et al. |
| 2021/0128165 A1 | 5/2021 | Pulugurtha et al. |
| 2021/0128167 A1 | 5/2021 | Patel et al. |
| 2021/0128168 A1 | 5/2021 | Nguyen et al. |
| 2021/0128169 A1 | 5/2021 | Li et al. |
| 2021/0129275 A1 | 5/2021 | Nguyen et al. |
| 2021/0153872 A1 | 5/2021 | Nguyen et al. |
| 2021/0169499 A1 | 6/2021 | Merritt et al. |
| 2021/0275184 A1 | 9/2021 | Hewitt et al. |
| 2021/0282789 A1 | 9/2021 | Vu et al. |
| 2021/0338247 A1 | 11/2021 | Gorochow |
| 2021/0346032 A1 | 11/2021 | Patterson et al. |
| 2022/0110710 A1 | 4/2022 | Rangwala et al. |
| 2022/0125567 A1 | 4/2022 | Center et al. |
| 2022/0192678 A1 | 6/2022 | Hewitt et al. |
| 2022/0202425 A1 | 6/2022 | Gorochow et al. |
| 2022/0249098 A1 | 8/2022 | Milhous et al. |
| 2022/0257258 A1 | 8/2022 | Hewitt et al. |
| 2022/0257260 A1 | 8/2022 | Hewitt et al. |
| 2022/0304696 A2 | 9/2022 | Rhee et al. |
| 2022/0304699 A1 | 9/2022 | Gorochow |
| 2022/0378435 A1 | 12/2022 | Dholakia et al. |
| 2023/0017191 A1 | 1/2023 | Gorochow et al. |

FOREIGN PATENT DOCUMENTS

| | | |
|---|---|---|
| DE | 102012016555 A1 | 2/2014 |
| DE | 102013006503 A1 | 7/2014 |
| EP | 0832607 A1 | 4/1998 |
| EP | 3146916 A1 | 3/2017 |
| EP | 2647343 B1 | 7/2017 |
| WO | WO1999/05977 A1 | 2/1999 |
| WO | WO2002/00139 A1 | 1/2002 |
| WO | WO2005107650 A2 | 11/2005 |
| WO | WO2008156464 A1 | 12/2008 |
| WO | WO2009055782 A1 | 4/2009 |
| WO | WO2009132045 A2 | 10/2009 |
| WO | WO2012009675 A2 | 1/2012 |
| WO | WO2013138615 A2 | 9/2013 |
| WO | WO2015057796 A1 | 4/2015 |
| WO | WO2015168249 A1 | 11/2015 |
| WO | WO2017/102804 A1 | 6/2017 |
| WO | WO2017/153603 A1 | 9/2017 |
| WO | WO2017/220400 A1 | 12/2017 |
| WO | WO2019038293 A1 | 2/2019 |
| WO | WO2020243039 A1 | 12/2020 |

OTHER PUBLICATIONS

Perez, M., Henkes, H., Bouillot, P., Brina, O., Slater, L., Pereira, V., "Intra-aneurysmal hemodynamics: evaluation of pCONus and pCANvas bifurcation aneurysm devices using DSA optical flow imaging", Journal of NeuroInterventional Surgery, Dec. 23, 2015, 6 pages, 10.1136/neurintsurg-2015-011927, Society of NeuroInterventional Surgery, Fairfax, USA.

Torii, R., Oshima, M., Kobayashi, T., Takagi, K., Tezduyar, T., "Fluid-structure interaction modeling of a patient-specific cerebral aneurysm: influence of structural modeling." Computational Mechanics 43: 151-159 (2008).

Control, etc. http://www.asianjns.org/articles/2012/7/4/images/AsianJNeurosurg_2012_7_4_159_106643_f7.jpg downloaded from internet Apr. 3, 2020.

Cerus https://neuronewsinternational-wpengine.netdna-ssl.com/wp-content/uploads/sites/3/2016/07/Cerus-Endovascular-Contour-300x194.jpg downloaded from internet Apr. 3, 2020.

Contour https://neuronewsinternational-wpengine.netdna-ssl.com/wp-content/uploads/sites/3/2017/06/Contour-e1497957260381-300x194.png downloaded from internet Apr. 3, 2020.

Medtronic https://evtoday.com/images/articles/2017-02/0217-endovascular-fig1.png downloaded from internet Apr. 3, 2020.

Bhogal, P., Udani, S., Cognard, C., Piotin, M., Brouwer, P., Sourour, N., Andersson, T., Makalanda, L., Wong, K., Fiorella, D., Arthur, A., Yeo, L., Soderman, M., Henkes, H., Pierot, L., "Endovascular flow disruption: where are we now?" Journal of Neurointerventional Surgery 11: 1024-1035 (2019).

PCT International Search Report and Written Opinion for PCT/US2022/013986, Galaxy Therapeutics, Inc., Forms PCT/ISA/220, 210, and 237 dated Jun. 2, 2022 (14 pages).

* cited by examiner

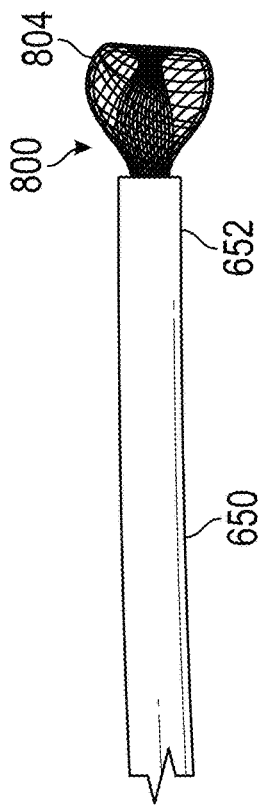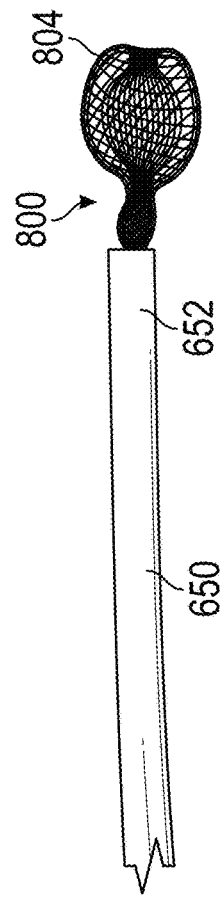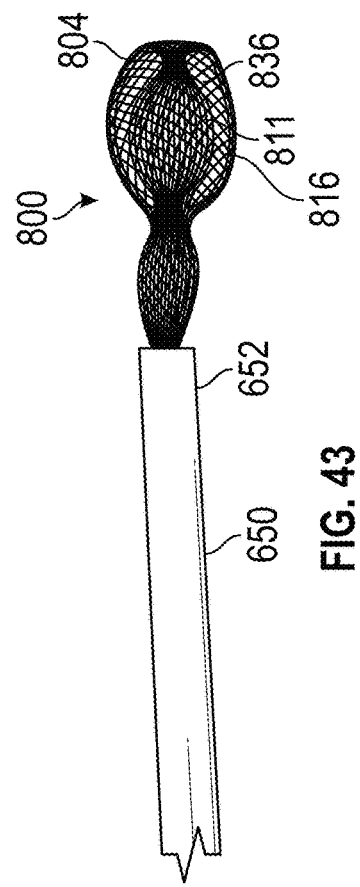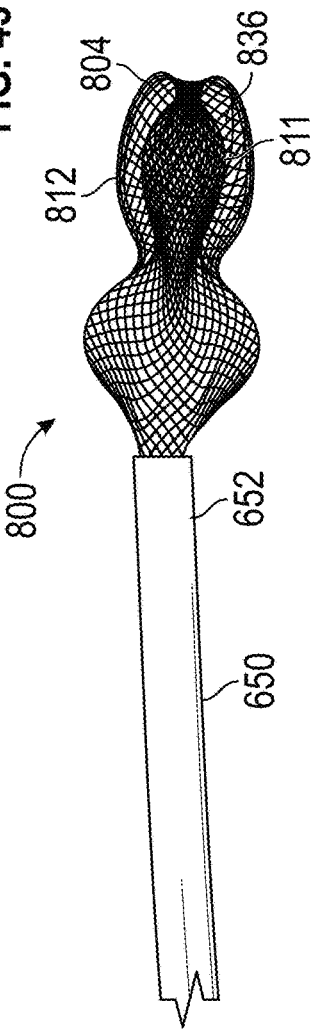

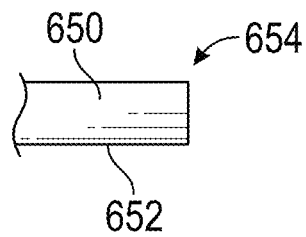
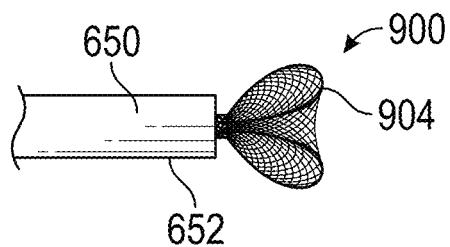
FIG. 49    FIG. 50
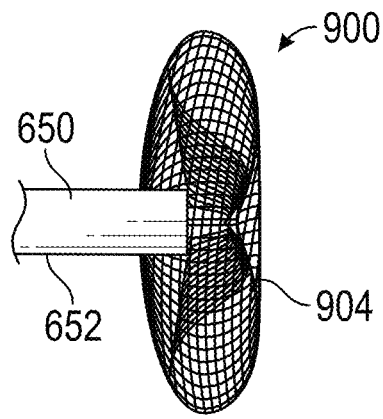
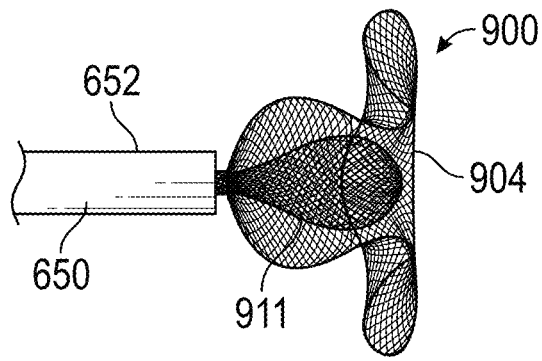
FIG. 51    FIG. 52
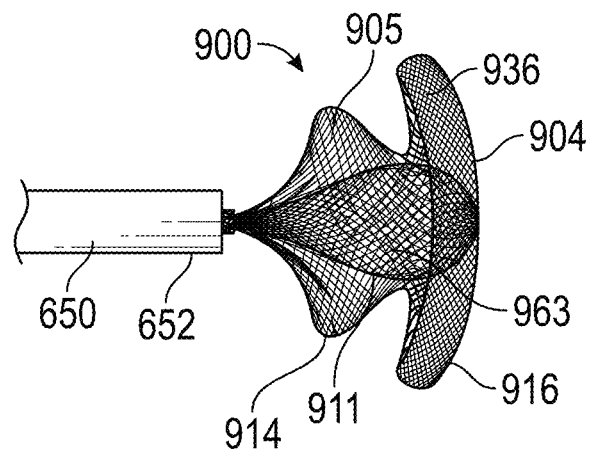
FIG. 53

SYSTEMS AND METHODS FOR TREATING ANEURYSMS

INCORPORATION BY REFERENCE TO ANY PRIORITY APPLICATIONS

This application is a continuation of international application no. PCT/US2022/013986, filed on Jan. 27, 2022, which claims the benefit of priority to U.S. Provisional Application No. 63/142,480, filed on Jan. 27, 2021, and U.S. Provisional Application No. 63/213,030, filed on Jun. 21, 2021, all of which are incorporated by reference in their entirety herein for all purposes. Priority is claimed pursuant to 35 U.S.C. § 120 and 35 U.S.C. § 119.

BACKGROUND OF THE INVENTION

Field of the Invention

The field of the invention generally relates to embolic devices for filling spaces in the vascular system, including cerebral aneurysms or left atrial appendages. In some case, the embolic devices may be used to embolize native vessels.

Description of the Related Art

An embolic device may be used as a stand-alone device to occlude and aneurysm, or may be used with an adjunctive device or material.

SUMMARY OF THE INVENTION

In one embodiment of the present disclosure, an apparatus for treating an aneurysm in a blood vessel includes an occlusion element configured to be releasably coupled to an elongate delivery shaft and configured to be delivered in a collapsed configuration through an inner lumen of a delivery catheter, the occlusion element including an inverted mesh tube having an outer layer and an inner layer, the outer layer transitioning to the inner layer at an inversion fold, wherein at least the outer layer is formed into a first expanded shape including: a smooth outer cylinder configured to engage a wall of an aneurysm throughout a 360° circumference; and a substantially distal-facing surface including one or more heat-formed undulations, the one or more undulations configured to apply a radial force on the wall of the aneurysm.

In another embodiment of the present disclosure, an apparatus for treating an aneurysm in a blood vessel includes an occlusion element configured to be releasably coupled to an elongate delivery shaft and configured to be delivered in a collapsed configuration through an inner lumen of a delivery catheter, the occlusion element including an inverted mesh tube having an outer layer and an inner layer, the outer layer transitioning to the inner layer at an inversion fold, wherein at least the outer layer is formed into a first expanded shape including an outer lateral surface extending around the occlusion element, and a substantially distal-facing surface including one or more heat-formed undulations, the one or more undulations configured to apply a radial force on a wall of an aneurysm.

In yet another embodiment of the present disclosure, an apparatus for treating an aneurysm in a blood vessel includes an occlusion element configured to be releasably coupled to an elongate delivery shaft and configured to be delivered in a collapsed configuration through an inner lumen of a delivery catheter, the occlusion element including an inverted mesh tube having an outer layer and an inner layer, the outer layer transitioning to the inner layer at an inversion fold, wherein at least the outer layer is formed into a first expanded shape having a first diameter, wherein the inner layer is formed into a second expanded shape contained within the first expanded shape, the second expanded shape having a second diameter.

In still another embodiment of the present disclosure, an occlusion device for treating an aneurysm in a blood vessel includes a body configured to be releasably coupled to an elongate delivery shaft and configured to be delivered in a collapsed configuration through an inner lumen of a delivery catheter, the body further configured to expand to an expanded configuration when delivered out of the inner lumen of the delivery catheter, the body including an inverted mesh tube having an outer layer and an inner layer, the outer layer transitioning to the inner layer at an inversion fold, wherein the outer layer includes a globular portion and wherein the inner layer includes a first proximal inner cover portion within a proximal end of the globular portion and wherein the inner layer further includes a distal columnar portion extending from the first proximal inner cover portion.

In yet another embodiment of the present disclosure, occlusion device for treating an aneurysm in a blood vessel includes a body configured to be releasably coupled to an elongate delivery shaft and configured to be delivered in a collapsed configuration through an inner lumen of a delivery catheter, the body further configured to expand to an expanded configuration when delivered out of the inner lumen of the delivery catheter, the body including an inverted mesh tube having an outer layer and an inner layer, the outer layer transitioning to the inner layer at an inversion fold, wherein the outer layer includes a first proximal cover portion having a cover diameter and a first distal globular portion extending distally from the cover portion, and wherein the inner layer includes a second proximal cover portion within the first proximal cover portion and a second distal globular portion within the first distal globular portion.

In still another embodiment of the present disclosure, an occlusion device for treating an aneurism in a blood vessel includes a body configured to be releasably coupled to an elongate delivery shaft and configured to be delivered in a collapsed configuration through an inner lumen of a delivery catheter, the body further configured to expand to an expanded configuration when delivered out of the inner lumen of the delivery catheter, the body including an inverted mesh tube having an outer layer and an inner layer, the outer layer transitioning to the inner layer at an inversion fold, wherein the outer layer includes a globular portion and wherein the inner layer includes a proximal inner cover portion within a proximal end of the globular portion and wherein the inner layer further includes a distal inner cover portion extending from the proximal inner cover portion, the distal portion having a significantly smaller diameter than the proximal inner cover portion.

BRIEF DESCRIPTION OF THE DRAWINGS

FIGS. 40-46 illustrate the deployment of the occlusion device of FIG. 38 from a delivery catheter.

FIGS. 49-56 illustrate the deployment of the occlusion device of FIG. 47 from a delivery catheter.

DETAILED DESCRIPTION OF THE ILLUSTRATED EMBODIMENTS

Figure 1:
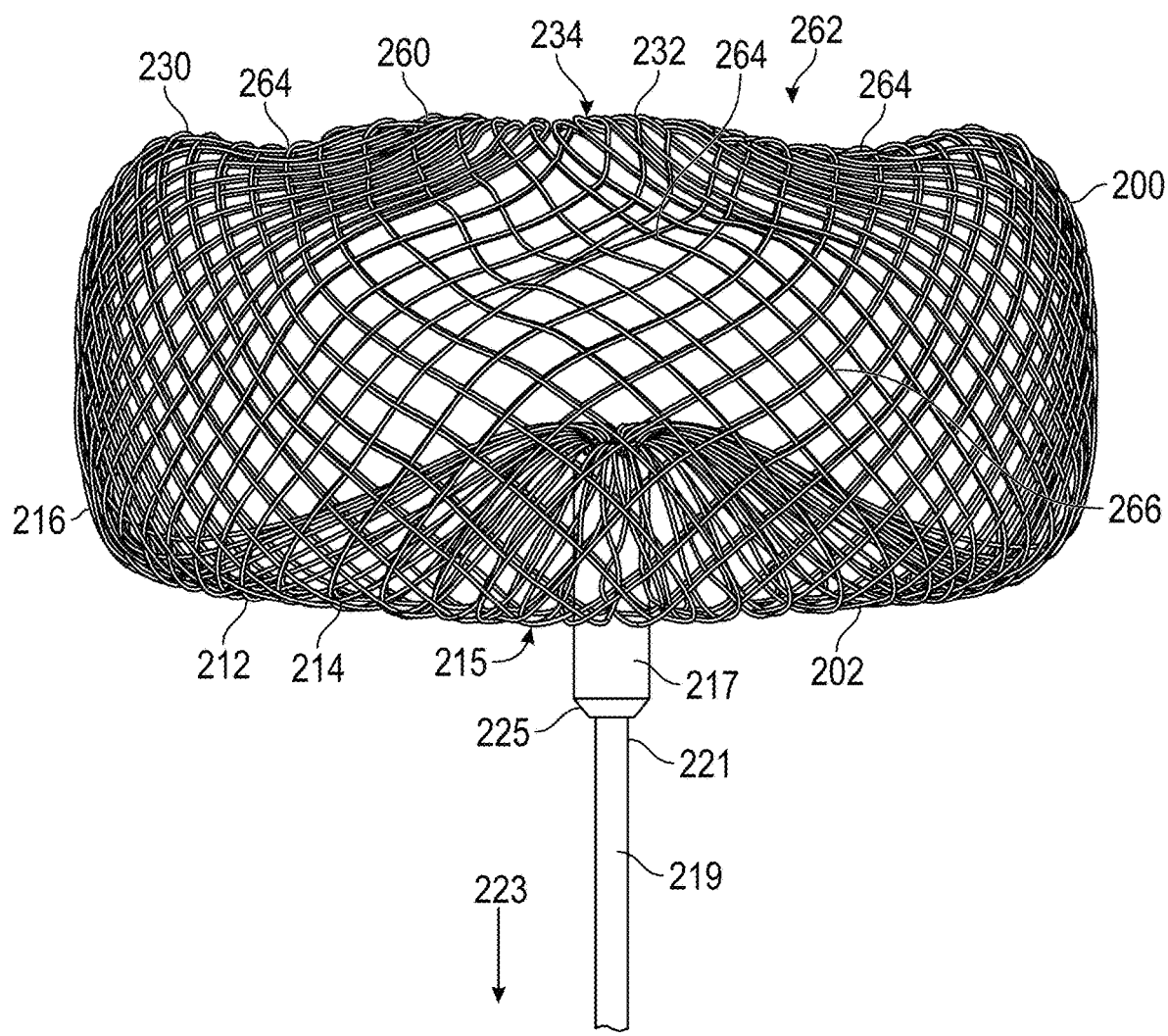
FIG. 1 is a perspective view of an occlusion device, according to an embodiment of the present disclosure.

Aneurysms are abnormal bulging or weakening of a blood vessel, often an artery, and can have many complications. A bulging of the blood vessel can disrupt or put pressure on surrounding tissues. Cerebral aneurysms can result in a variety of side effects, such as impaired vision, impaired speech, impaired balance, etc. Further, the aneurysm creates a volume that is not along the main flow path of the blood through the blood vessel. It therefore can serve as a location for blood to become stagnant and, due to swirling eddy currents, can contribute to the formation of a thromboembolism. If an aneurysm ruptures, it can cause severe internal bleeding, which in cerebral arteries can often become fatal.

Aneurysms can be treated externally with open surgery. Such procedures typically involve closing off the entrance or "neck" of the aneurysm with a device such as vascular clip, clamp or a ligature. However, such open surgical procedures can be highly invasive and may lead to trauma to the adjacent tissue and other side effects.

Aneurysms can also be treated through endovascular procedures. In one procedure, detachable lengths of wires (e.g., coils) are inserted into the interior volume of the aneurysm using a catheter. The coils are intended to fill the volume of the aneurysm to decrease the flow of blood into the aneurysm, inducing stagnation of flow and stimulate clotting within the aneurysm. In settings of large cerebral aneurysms, filling of the aneurysm with multiple coils can lead to mass effect that may induce brain swelling and be an independent cause for new symptoms. In another procedure, for aneurysms with a relatively large neck, the adjunctive use of stents assists with the retention of the coils within the aneurysm. This approach may have a contraindication to being used when treating ruptured aneurysm, due to the need for additional anti-thrombotic medications. In another procedure, the coils are held in the volume of the aneurysm with a temporary balloon that is inflated in the blood vessel. The balloon is deflated and removed once the mass of coils is secured. In still another procedure, a stent device is placed in the artery to promote flow of blood past the aneurysm. This leads to stagnation of the blood within the aneurysm and thrombosis inside the aneurysm volume. However, a side branch of a main artery in which the stent device is placed may become trapped or "jailed," which can impede access to the side branch. In other instances, the side branch can become clotted off, possibly causing a stroke. Additionally, such a procedure generally requires the use additional anti-thrombotic medications, which limits the use of such devices in the setting of treatment of ruptured aneurysms. The stent device is often formed with a relatively tight weave. While the tight weave increases the effectiveness of the stent device in diverting the blood flow, it also impedes or prevents access to the volume of the aneurysm or the jailed artery. In the event that the aneurysm fails to clot, the obstruction of the aneurysm by the stent device prevents the possibility of placing embolic devices inside the aneurysm. Additional procedures such as the placement of additional stents or open surgery may then be required to treat the residual.

Procedures that involve packing the volume of the aneurysm can suffer from several common shortcomings. First, it can take many coils of wire to fill the volume of the aneurysm, which is time consuming and increases the time it takes to complete the procedure. Further, the coils may be compacted over time to occupy a smaller percentage of the total volume of the aneurysm. A great enough compaction of the coils can be considered a recurrence of the aneurysm and may require further treatment.

Figure 2:
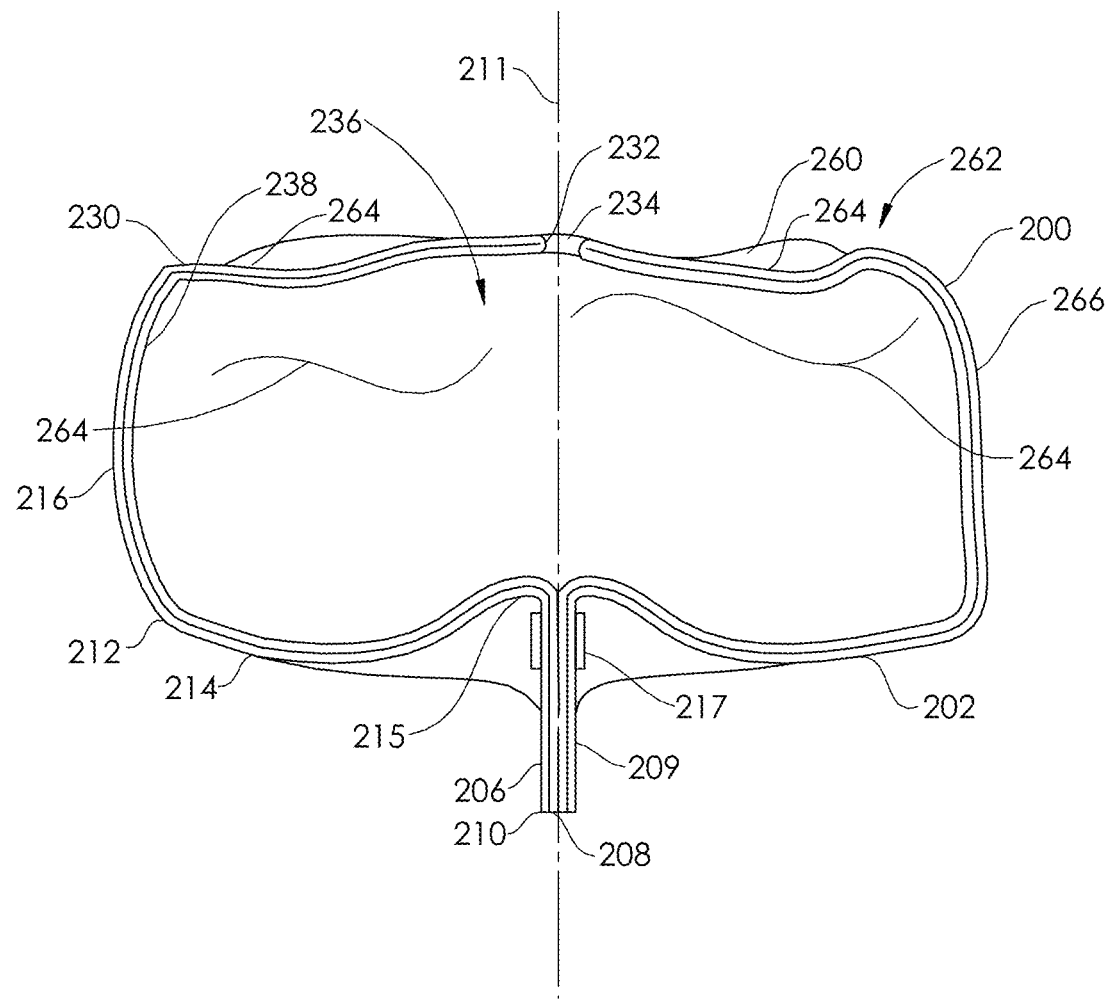
FIG. 2 is a sectional view of the occlusion device of FIG. 1.

FIG. 1 illustrates an occlusion device 200 configured for placement within an aneurysm. The occlusion device 200 comprises a proximal end 202 and a distal end 230, and is constructed of a single, continuous dual layer mesh 266. Turning to FIG. 2, the occlusion device 200 is constructed from an inverted mesh tube 206 having a first end 208, a second end 210, and a wall 209. The inverted mesh tube 206 extends on an outer layer 212 of the inverted mesh tube 206, from the second end 210 past a proximal concavity 215 along a convex proximal surface 214 and along a smooth cylindrical section 216 to the distal end 230 of the occlusion device 200. The smooth cylindrical section 216 is configured to provide full 360° contact with the inner wall of an aneurysm (around the longitudinal axis 211 of the occlusion device 200), to form a cylindrical closure region with the aneurysm. The outer diameter of the smooth cylindrical section 216 may be between about 3 mm to about 15 mm, or between about 3 mm and about 7 mm. At the distal end 230, the wall 209 is inverted inwardly at an inversion fold 232, which creates a distal orifice 234 and an internal volume 236. The wall 209 transitions at the inversion fold 232 from the outer layer 212 to an inner layer 238 which follows the contours of the outer layer 212 from the distal orifice 234 to the first end 208. The inner layer 238 follows the contours of the distal end 230, the smooth cylindrical section 216, the convex proximal surface 214, and the proximal concavity 215. In the embodiment of FIG. 2, the outer layer 212 and the inner layer 238 are substantially flush in relation to each other. The occlusion device 200 is fabricated as an inverted mesh tube 206 having a simple straight elongate configuration, and is subsequently formed into the shape shown in FIGS. 1 and 2 and heat set into this shape. For example, the occlusion device 200 can be constructed as a single layer mesh tube formed of at least some nickel-titanium alloy filaments, and then inverted on itself. The inverted mesh tube 206 can then be placed into a die or mold comprising one or more pieces, to hold it in the shape of the occlusion device 200. Then, the occlusion device 200 can be subjected to an elevated temperature and then cooled, to lock in the shape, resulting in an occlusion device 200 having at least some superelastic properties. The occlusion device 200 is configured to be compressed or compacted within the lumen 148 of a delivery catheter 150 (e.g., microcatheter) (see FIG. 7).

In some embodiments, the occlusion device 200 may comprise some nickel-titanium alloy filaments and some radiopaque elements, comprising platinum, gold, tantalum, or alloys of any of these or other radiopaque materials. In some embodiments, the filaments may comprise drawn filled tubes, such as those comprising a nickel-titanium alloy outer wall and a platinum core. The radiopaque material allows the occlusion device 200 to be visible on radiographs or fluoroscopy. The occlusion device 200 may be configured by controlling how much radiopaque material is used, by either the ratio of radiopaque filaments to non-radiopaque filaments, or by the amount of platinum core in the drawn filled tubes. In this manner, the occlusion device 200 can be selectively fabricated to be sufficiently visible, but not over visible, e.g., overly bright, such that other objects are obscured. In some embodiments, whether any of the filaments comprise radiopaque materials or not, a marker band 217 can be attached adjacent the proximal end 202 by adhesive or epoxy bonding, or swaging, welding or other mechanical attachment. As shown in FIGS. 1-2, the marker band 217 can be configured to partially or completely reside within the proximal concavity 215 of the expanded occlusion device 200. The occlusion device 200 is detachably coupled at a detachable joint 225, at or adjacent its proximal end 202, to a pusher wire 219 having a distal end 221 and a proximal end 223. The detachable joint 225 can comprise one of a number of detachment systems, including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems. In any of the embodiments disclosed herein, alternative detachable joint may be employed, such as the detachable joints disclosed in U.S. Pat. No. 11,058,431, issued Jul. 13, 2021, and entitled "Systems and Methods for Treating Aneurysms" and in U.S. Pat. No. 10,856,880, issued Dec. 8, 2020, and entitled "Systems and Methods for Treating Aneurysms," both of which are hereby incorporated by reference in their entirety for all purposes.

The occlusion device 200 is heat set into the shape shown in FIGS. 1-2 using male and/or female forms or molds, to create a wavy shape 262 on a distal surface 260 of the distal end 230. The distal surface 260 may be generally thought of as the "end" of a cylinder, although the shape of the distal surface 260 is not planar. The wavy shape 262 includes a series of curvilinear contours 264 along the distal surface 260. The male and/or female forms or molds have mating shapes such that the expanded mesh is held with the distal surface 260 in these contours during the heat set process. The forms or molds are then removed after the shape memory/nickel-titanium mesh 266 has been heated to a set temperature and then cooled. The combination of the smooth circumference of the smooth cylindrical section 216 and the wavy shape 262 of the distal surface 260 in a single occlusion device 200 provides an implant that is configured to seal or close the aneurysm wall, but is also configured to provide an increased radial force to allow stabilization of the implant within the aneurysm. The curvilinear contours 264 in the mesh 266 provide a spring-like bias in a radial direction, that would not be present or would be less present if the distal surface 260 were instead formed as a flat disk or planar shape. The curvilinear contours 264 provide radial forces to create a good anchor against the wall of the aneurysm, which, along with the contact of the smooth cylindrical section 216, helps prevent endoleak, by forming an effective closure.

The curvilinear contours 264 may take a wide variety of forms, when described in a two-dimensional basis (e.g, in cross-section) or when described in a three-dimensional basis (surface contour). In some embodiments, the curvilinear contours 264 may comprise true wave shapes, and in other embodiments, the curvilinear contours 264 may comprise pseudo-wave shapes. In both cases, the shape may be described as "wavy" or "undulating." In the embodiments wherein a true wave is represented in the shape (e.g., along a particular axis), the wave may in some embodiments be sinusoidal, and in other embodiments be non-sinusoidal. In some embodiments, the wave-shape may be continuous (e.g., across the surface), and in other embodiments, the wave-shape may be discontinuous or interrupted. In some embodiments, the wave-shape may increase in frequency in one direction (or likewise, decreasing in frequency in the other direction); for example, along a particular axis or along a particular transverse plane. In some embodiments, the wave-shape may maintain a substantially consistent amplitude (e.g., peak height) throughout, and in other embodiments, the amplitude may have a "damped" appearance and may increase or decrease along a particular axis or along a particular transverse plane. In some embodiments, the three-dimensional surface contour of the distal surface 260 may comprise a section comprising two or more wave shapes having a convex or concave surface between them. In some embodiments, the two or more wave shapes may be substantially parallel to each other, or may be substantially non-parallel to each other. For example, a convex wave peak may be adjacent a concave surface. Or, a concave peak may be adjacent a convex surface.

Figure 3A:
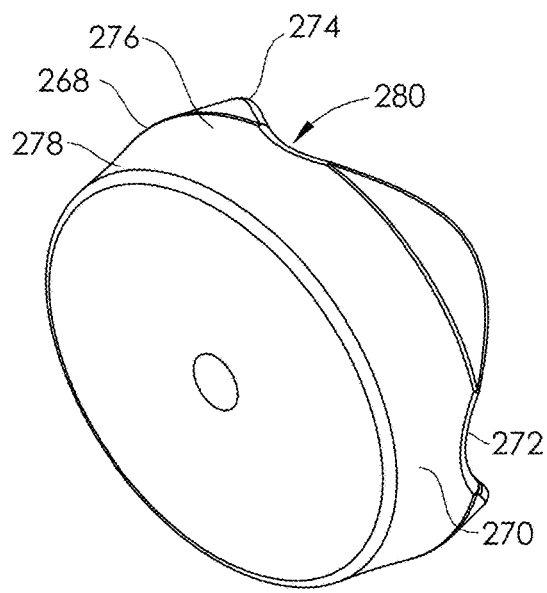
FIG. 3A is a perspective view of a first alternative shape of an occlusion device, according to an embodiment of the present disclosure.

FIGS. 3A-6B illustrate occlusion devices similar to the occlusion device 200 of FIGS. 1-2, but with different shapes and dimensions. FIGS. 3A-3B illustrate an occlusion device 268 having a ratio of smooth cylindrical section 270 height $H_C$ to total height $H_T$ (ratio=$H_C/H_T$) equal to between about 0.42 and about 0.48, or equal to about 0.45. The occlusion device 268 has a ratio of curvilinear contour 272 height $H_W$ to total height $H_T$ (ratio=$H_W/H_T$) equal to between about 0.52 and about 0.58, or equal to about 0.55. The occlusion device 268 has a curvilinear contour 272 that extends around an outer circumference of the distal end 274. A maximum diameter $D_M$ of the occlusion device 268 occurs at an upper extreme 276 of the smooth cylindrical section 270. A minimum diameter $D_m$ of the occlusion device 268 occurs at a lower extreme 278 of the smooth cylindrical section 270. Thus, the smooth cylindrical section 270 is a frustoconical surface providing a tapering diameter, that tapers up (increasingly in diameter) toward the curvilinear contour 272. The occlusion device 268 has a ratio of total height $H_T$ to maximum diameter $D_M$ (ratio=$H_T/D_M$) equal to between about 0.25 and about 0.57, or between about 0.35 and about 0.49, or equal to about 0.42. The occlusion device 268 is formed using a female form or mold that engages the distal surface 280.

Figure 4A:
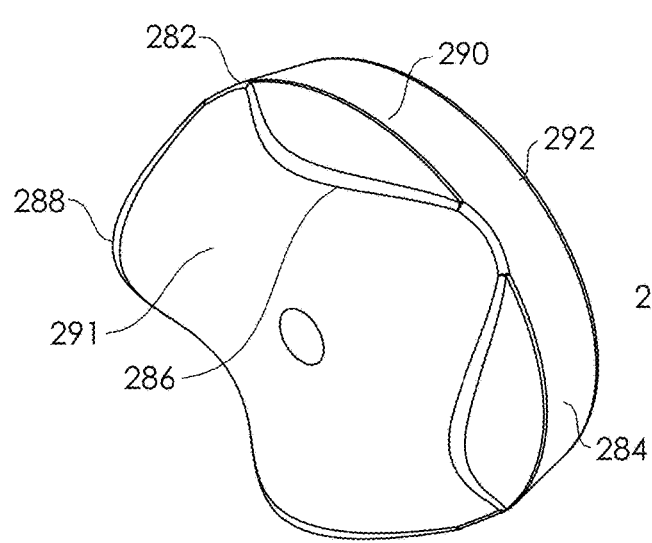
FIG. 4A is a perspective view of a second alternative shape of an occlusion device, according to an embodiment of the present disclosure.
Figure 4B:
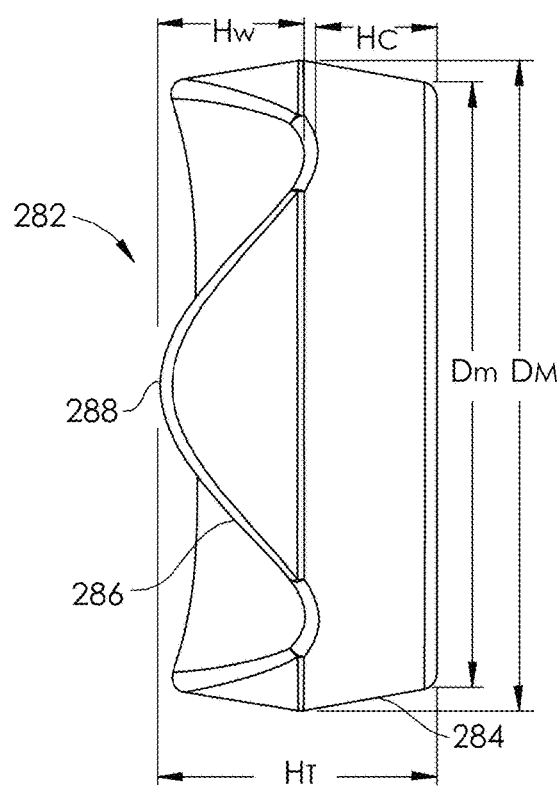
FIG. 4B is a side view of the occlusion device of FIG. 4A.

FIGS. 4A-4B illustrate an occlusion device 282 having a ratio of smooth cylindrical section 284 height $H_C$ to total height $H_T$ (ratio=$H_C/H_T$) equal to between about 0.47 and about 0.55, or equal to about 0.50. The occlusion device 282 has a ratio of curvilinear contour 286 height $H_W$ to total height $H_T$ (ratio=$H_W/H_T$) equal to between about 0.47 and about 0.55, or equal to about 0.50. The occlusion device 282 has a curvilinear contour 286 that extends around an outer circumference of the distal end 288. A maximum diameter $D_M$ of the occlusion device 282 occurs at an upper extreme 290 of the smooth cylindrical section 284. A minimum diameter $D_m$ of the occlusion device 282 occurs at a lower extreme 292 of the smooth cylindrical section 284. Thus, the smooth cylindrical section 284 is a frustoconical surface providing a tapering diameter, that tapers up toward the curvilinear contour 286. The occlusion device 282 has a ratio of total height $H_T$ to maximum diameter $D_M$ (ratio=$H_T/D_M$) equal to between about 0.25 and about 0.57, or between about 0.36 and about 0.50, or equal to about 0.41. The occlusion device 282 is formed using a male form or mold that engages the distal surface 291.

Figure 5A:
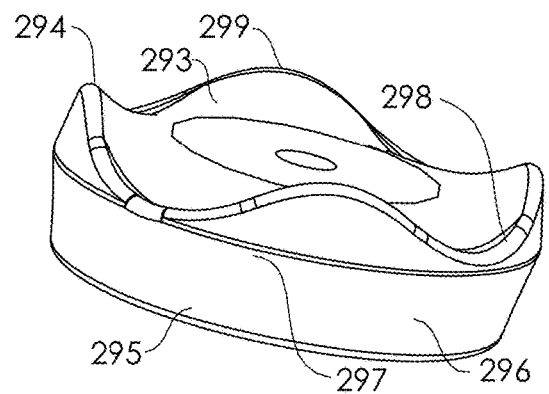
FIG. 5A is a perspective view of a third alternative shape of an occlusion device, according to an embodiment of the present disclosure.
Figure 5B:
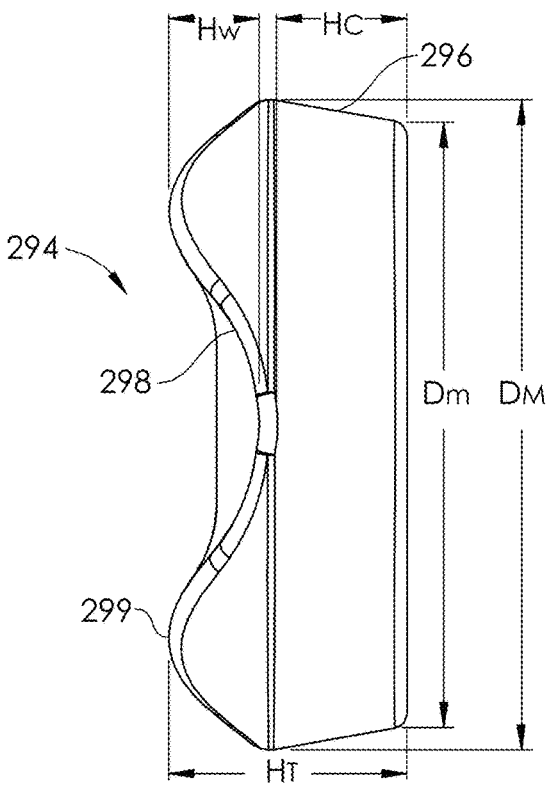
FIG. 5B is a side view of the occlusion device of FIG. 5A.

FIGS. 5A-5B illustrate an occlusion device 294 having a ratio of smooth cylindrical section 296 height $H_C$ to total height $H_T$ (ratio=$H_C/H_T$) equal to between about 0.59 and about 0.66, or equal to about 0.625. The occlusion device 294 has a ratio of curvilinear contour 298 height $H_W$ to total height $H_T$ (ratio=$H_W/H_T$) equal to between about 0.34 and about 0.41, or equal to about 0.375. The occlusion device 294 has a curvilinear contour 298 that extends around an outer circumference of the distal end 299. A maximum diameter $D_M$ of the occlusion device 294 occurs at an upper extreme 297 of the smooth cylindrical section 296. A minimum diameter $D_m$ of the occlusion device 294 occurs at a lower extreme 295 of the smooth cylindrical section 296. Thus, the smooth cylindrical section 296 is a frustoconical surface providing a tapering diameter, that tapers up toward the curvilinear contour 298. The occlusion device 294 has a ratio of total height $H_T$ to maximum diameter $D_M$ (ratio=$H_T/D_M$) equal to between about 0.20 and about 0.52, or between about 0.31 and about 0.45, or equal to about 0.36. The occlusion device 294 is formed using a female form or mold that engages the distal surface 293.

Figure 6A:
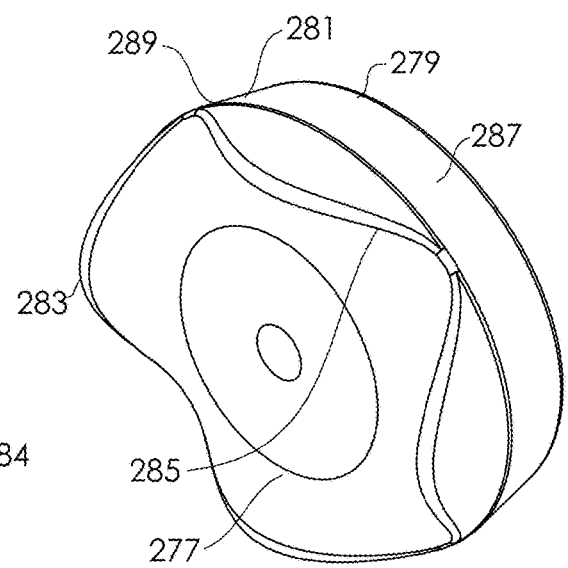
FIG. 6A is a perspective view of a fourth alternative shape of an occlusion device, according to an embodiment of the present disclosure.
Figure 6B:
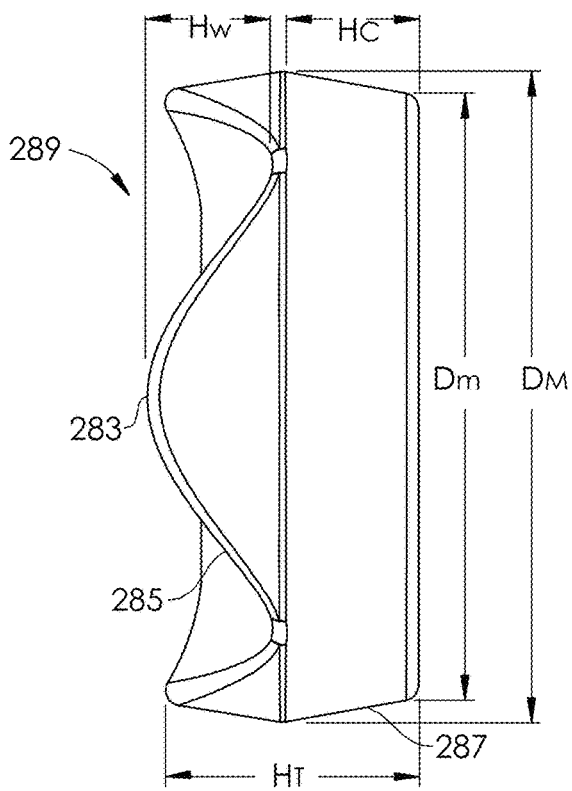
FIG. 6B is a side view of the occlusion device of FIG. 6A.

FIGS. 6A-6B illustrate an occlusion device 289 having a ratio of smooth cylindrical section 287 height $H_C$ to total height $H_T$ (ratio=$H_C/H_T$) equal to between about 0.40 and about 0.46, or equal to about 0.43. The occlusion device 289 has a ratio of curvilinear contour 285 height $H_W$ to total height $H_T$ (ratio=$H_W/H_T$) equal to between about 0.47 and about 0.55, or equal to about 0.50. The occlusion device 289 has a curvilinear contour 285 that extends around an outer circumference of the distal end 283. A maximum diameter $D_M$ of the occlusion device 289 occurs at an upper extreme 281 of the smooth cylindrical section 287. A minimum diameter $D_m$ of the occlusion device 289 occurs at a lower extreme 279 of the smooth cylindrical section 287. Thus, the smooth cylindrical section 287 is a frustoconical surface providing a tapering diameter, that tapers up toward the curvilinear contour 285. The occlusion device 289 has a ratio of total height $H_T$ to maximum diameter $D_M$ (ratio=$H_T/D_M$) equal to between about 0.25 and about 0.57, or between about 0.37 and about 0.51, or equal to about 0.42. The occlusion device 289 is formed using a male form or mold that engages the distal surface 277.

Figure 3B:
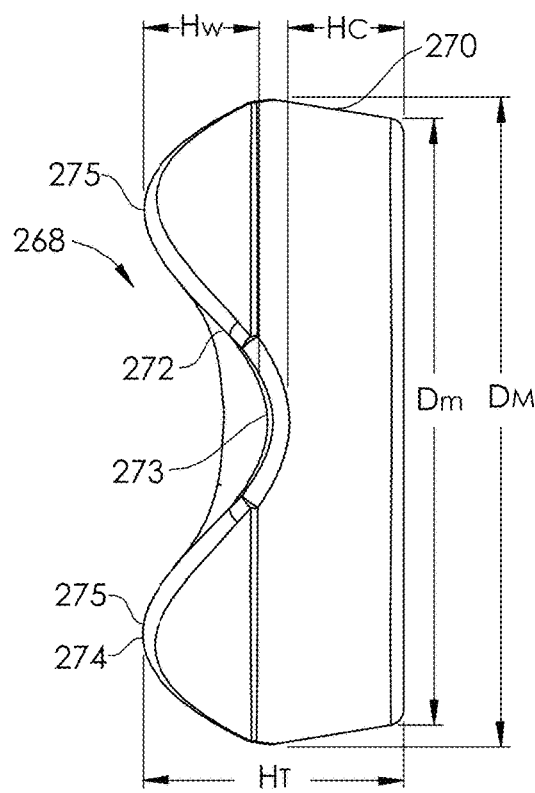
FIG. 3B is a side view of the occlusion device of FIG. 3A.

The occlusion devices 268, 282, 294, 289 of FIGS. 3A-6B each comprise curvilinear contours 272, 286, 298, 285 having four peaks 275 and four valleys 273 (see FIG. 3B). However, in alternative embodiments, the curvilinear contours may comprise two or more peaks 275/two or more valleys 273 or three or more peaks 275/three or more valleys 273, or four or more peaks 275/four or more valleys 273, or five or more peaks 275/five or more valleys 273, or more. The ratio of curvilinear contour height $H_W$ to total height $H_T$ (ratio=$H_W/H_T$) may be between about 0.10 to about 0.90, or about 0.25 to 0.75, or about 0.30 to about 0.60, or about 0.40 to about 0.60. The total height $H_T$ may be between about 1 mm and about 10 mm, or between about 2 mm and about 6 mm, or between about 2 mm and about 5 mm. Though the curvilinear contours 272, 286, 298, 285 of the occlusion devices 268, 282, 294, 289 extend around an outer circumference of the distal end, other embodiments, may have curvilinear contours that extend across the distal surface as diameters, radii, partial radial lines, chords, or partial chords. In some embodiments, the curvilinear contours may even follow a secondary curve, such that they trace a non-planar path.

Figure 7:
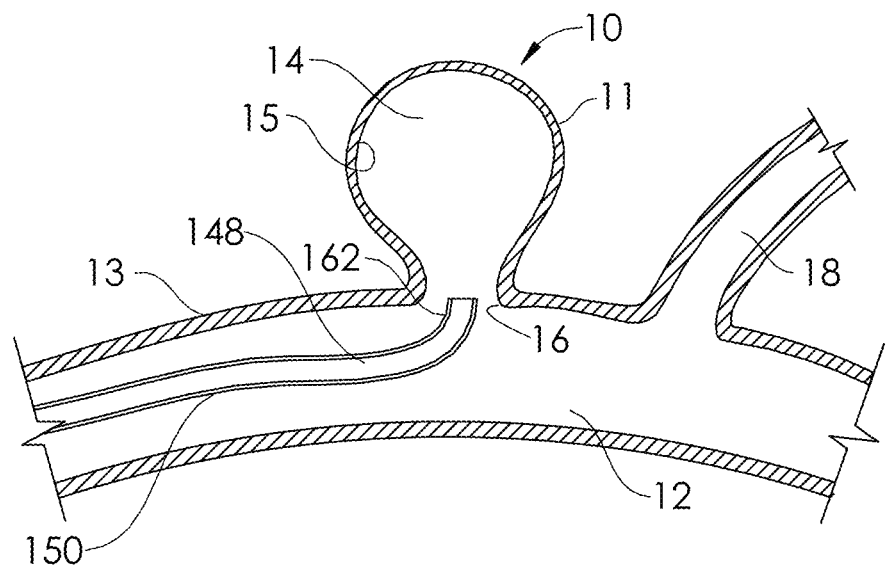
FIGS. 7-10 illustrate the implantation of the occlusion device of FIG. 1 in an aneurysm of a blood vessel of a patient.

In FIGS. 7-10, an aneurysm 10 having a neck portion 16 is shown. The occlusion device 200 is shown in use being implanted by a user (e.g., physician) into the aneurysm 10 through the delivery catheter 150 to disrupt or halt the flow of blood flow between the blood vessel 12 and the internal volume 14 of the aneurysm, thereby reducing the likelihood that the aneurysm 10 will rupture; or, if the aneurysm was previously ruptured, reducing the likelihood of rerupture. The occlusion device 200 is configured to be low profile device, minimizing disruptions to surrounding bodies, such as a side branch 18 of the blood vessel 12. The blood vessel 12 has a blood vessel wall 13 and the aneurysm 10 has an aneurysm wall 11. In FIG. 7, the delivery catheter 150 is advanced through a sheath and/or guiding catheter (not shown) through a puncture or cutdown in a peripheral blood vessel, such as a femoral artery, a brachial artery, or a radial artery. The distal end 162 of the delivery catheter 150 may be shaped with a curve, as shown, either by the manufacturer, or prior to the procedure by the user, in order to allow for improved backup support when delivering the occlusion device 200. The distal end 162 of the delivery catheter 150 is placed adjacent the neck portion 16 of the aneurysm 10. The delivery catheter 150 may be advanced over a guidewire (not shown) that is extended through the lumen 148. The guidewire may then be removed, leaving the lumen 148 as a delivery conduit and the delivery catheter 150 as a support column.

Figure 8:
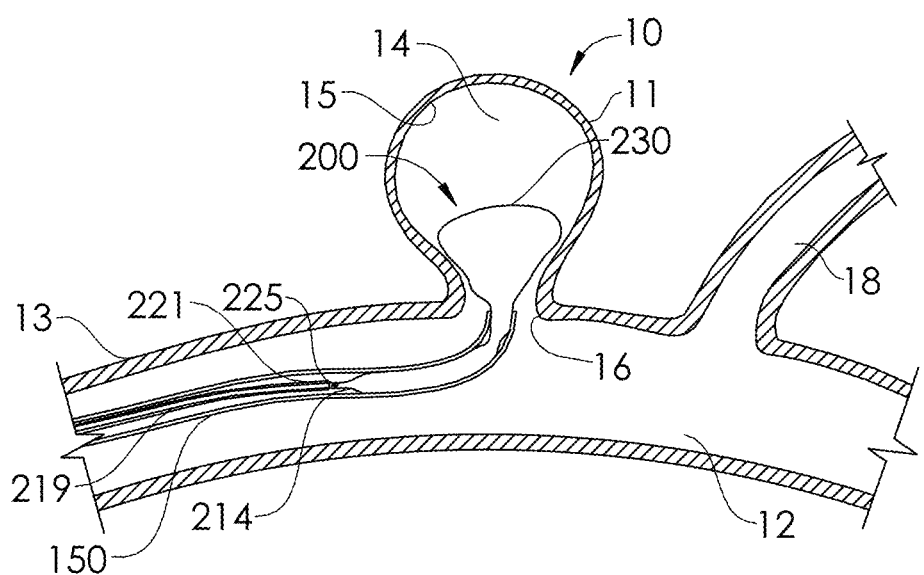
Figure 9:
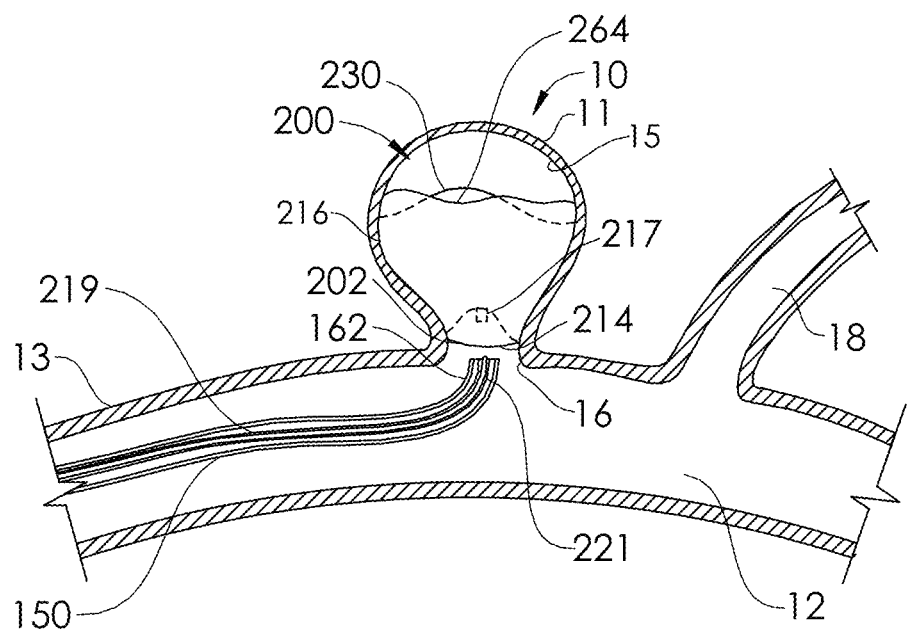

In FIG. 8, the occlusion device 200 is advanced through the lumen 148 of the delivery catheter 150, as described, and the distal end 230 of the occlusion device 200 is advanced out of the lumen 148 and into the internal volume 14 of the aneurysm 10. The distal end 230 is the first portion of the occlusion device 200 that exits the lumen 148 and thus is the first portion of the occlusion device to enter the aneurysm 10. In FIG. 9, the occlusion device 200 is shown in a substantially expanded configuration within the internal volume 14 of the aneurysm 10. The convex proximal end 214 is expanded within the aneurysm 10, and covers the neck portion 16 of the aneurysm.

Figure 10:
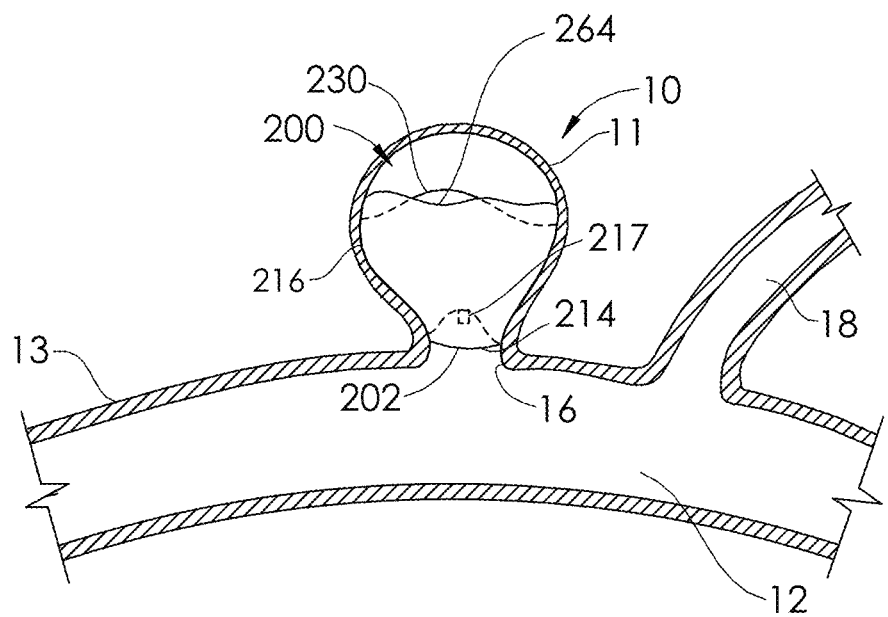

Also, in FIG. 9, the detachable joint 225 (see FIG. 8) has been detached, and thus, the distal end 221 of the pusher wire 219 can be pulled into the lumen 148 of the delivery catheter 150. In some embodiments, the delivery catheter 150 is maintained over the detachable joint 225 during the detachment procedure, to further protect the aneurysm 10. In FIG. 10, the delivery catheter 150 is removed, and the deployed occlusion device 200 is in place to begin to occlude the internal volume 14 of the aneurysm. The curvilinear contours 264 serve to force the smooth cylindrical section 216 radially against the wall 11 of the aneurysm 10, with the convex proximal surface 214 positioned around or against the neck portion 16 and/or against the interior surface 15. The dual layer of mesh in the proximal end 202 aids in the disruption of blood flow into the aneurysm 10, thus causing thrombosis to isolate the internal volume 14 of the aneurysm 10 from blood flow through the blood vessel 12. The curvilinear contours 264 can also help protect against undesired longitudinal (axial) compaction of the expanded occlusion device 200 over time, because the spring-like action of the multiple contours 264 serve as a greater resistance to compaction than a single, flat surface or single, convex surface. Braided aneurysm occlusion devices can often compact after many thousands or millions of heartbeats, and thus thousands or millions of cycles of systolic pressure. The cycles can cause deformation that shortens or otherwise compresses the devices. The curvilinear contours 264 serve to maintain the shape of the outer layer 212.

Figure 11:
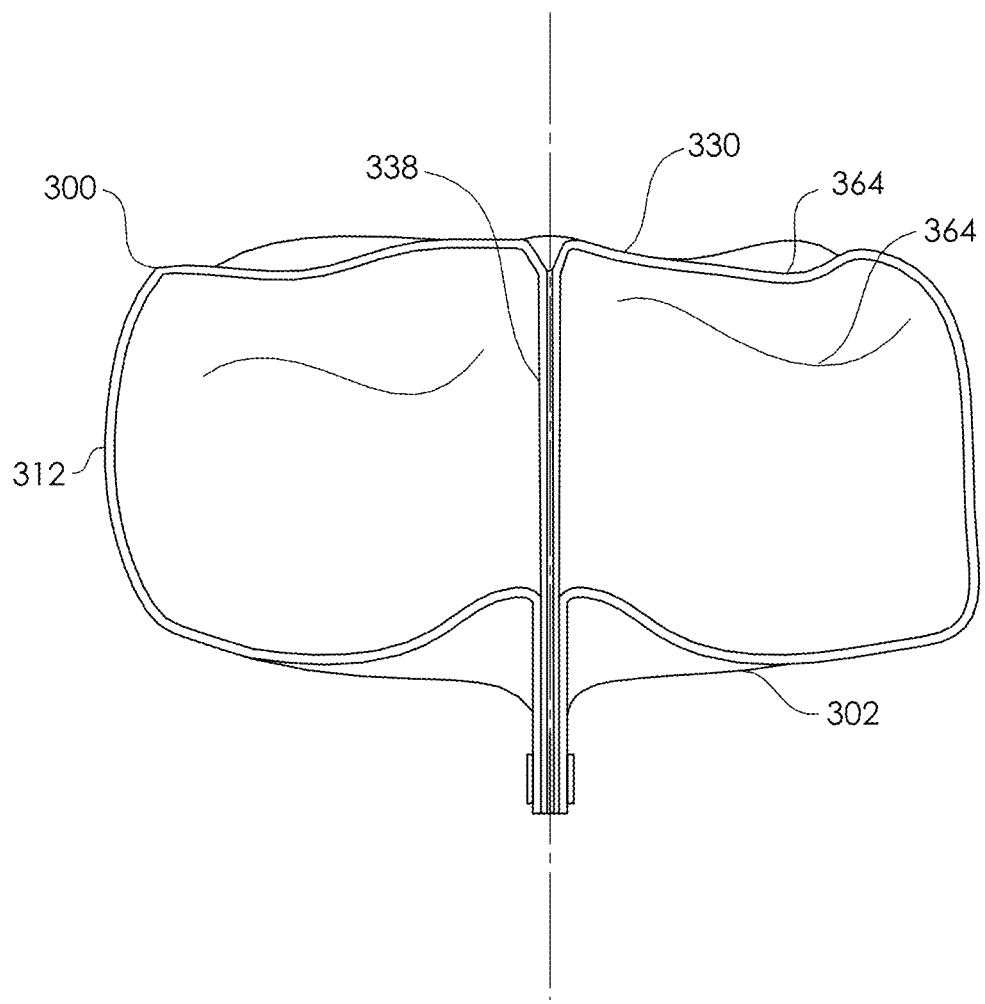
FIG. 11 is a sectional view of an alternative occlusion device, according to an embodiment of the present disclosure.

An alternative embodiment of the occlusion devices 200, 268, 282, 294, 289 from FIGS. 1-6B is illustrated in FIG. 11. Occlusion device 300 is similar to the occlusion device 200, including the curvilinear contours 364 at the distal end 330, however the inner layer 338 does not follow the contours of the outer layer 312, but instead is a substantially straight tubular column. This column may be the outer diameter of the original tubular mesh (as braided), or may be an expanded diameter (as heat formed). The outer diameter may also be minimized by reducing it via axial stretching of the inner layer 338 of the braided tube prior to heat forming. The inner layer 338 can provide additional column strength and longitudinal support, which can help to apply a generally longitudinal force against the aneurysm neck portion 16 with the proximal end 302. By pulling the expanded occlusion device 300 proximally, the outer layer 312 engages and grips the interior surface 15 of the aneurysm 10, allowing the column-shaped inner layer 338 to maintain the longitudinal force on the neck portion 16 of the aneurysm 10.

Figure 12A:
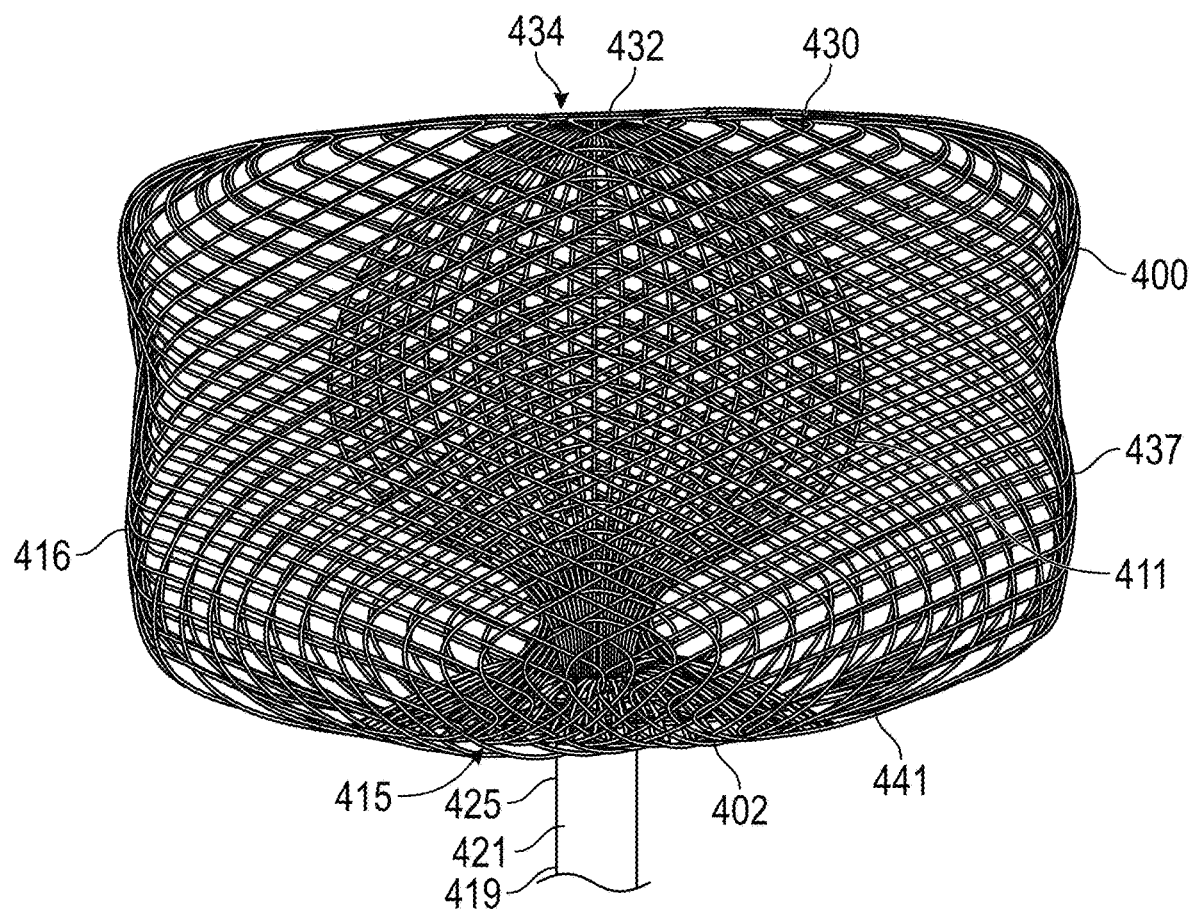
FIG. 12A is a perspective view of an occlusion device, according to an embodiment of the present disclosure.
Figure 12B:
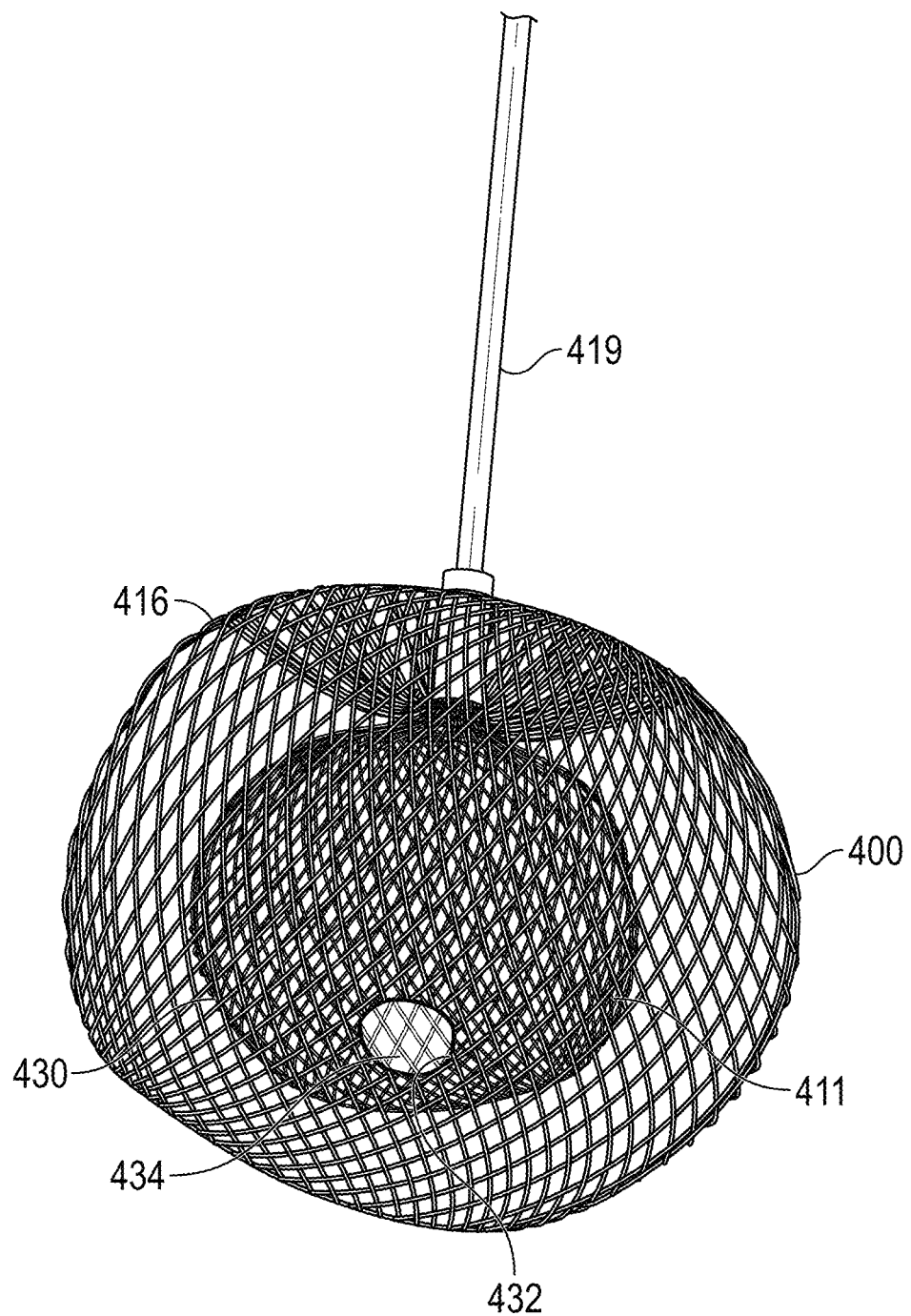
FIG. 12B is another perspective view of the occlusion device of FIG. 12A.
Figure 13:
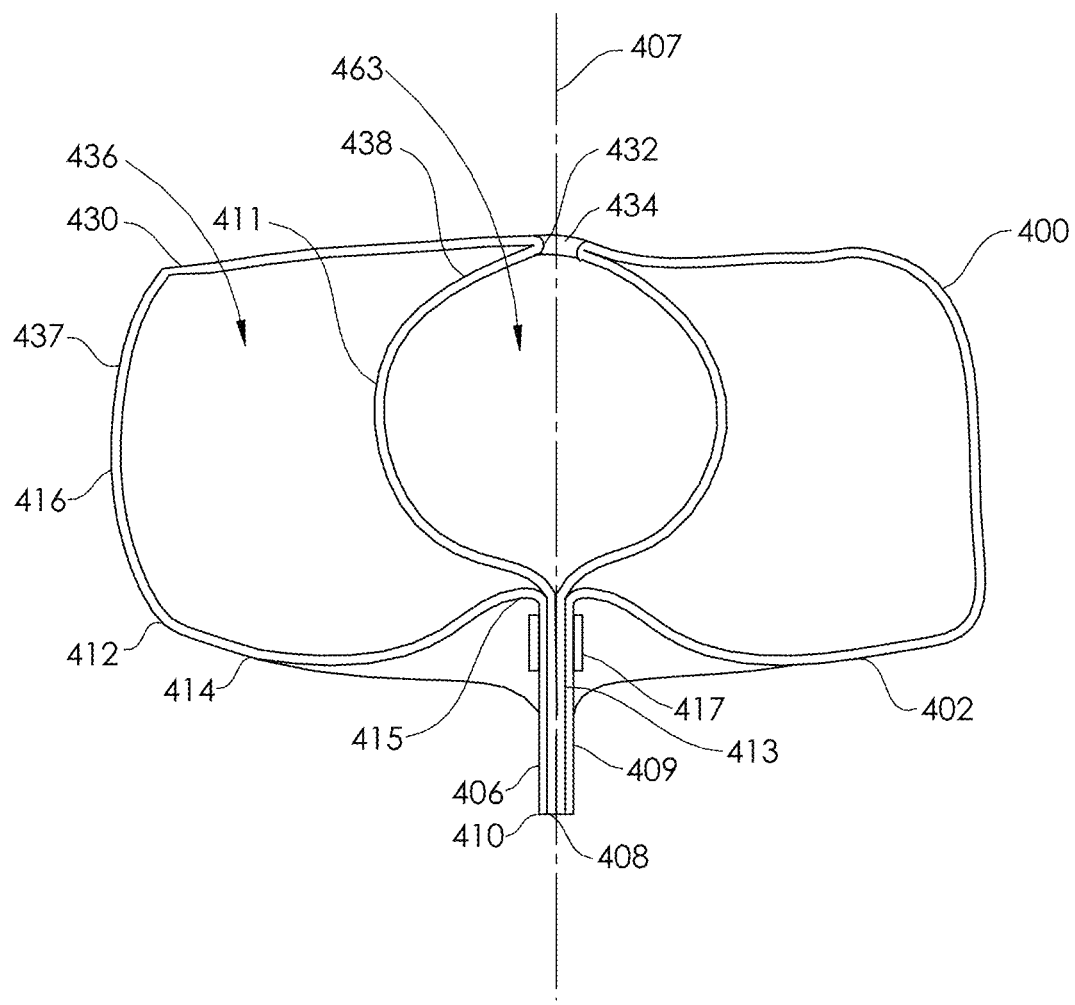
FIG. 13 is a sectional view of the occlusion device of FIG. 12A.

FIGS. 12A and 12B illustrate an occlusion device 400 configured for placement within an aneurysm. The occlusion device 400 comprises a proximal end 402 and a distal end 430, and is constructed of a single, continuous dual layer mesh. Turning to FIG. 13, the occlusion device 400 is constructed from an inverted mesh tube 406 having a first end 408, a second end 410, and a wall 409. The inverted mesh tube 406 extends on an outer layer 412 from the second end 410 past a proximal concavity 415 along a convex proximal surface 414 and along a smooth cylindrical section 416 to the distal end 430 of the occlusion device 400. The smooth cylindrical section 416 is configured to provide full 360° contact with the inner wall of an aneurysm (around the longitudinal axis 407 of the occlusion device 400), to form a cylindrical closure region with the aneurysm. The outer diameter of the smooth cylindrical section 416 may be between about 3 mm to about 15 mm, or between about 3 mm and about 7 mm. At the distal end 430, the wall 409 is inverted inwardly at an inversion fold 432, which creates a distal orifice 434 and a first internal volume 436 and a second internal volume 463. The second internal volume 463 is inside a formed ball 411 and the first internal volume 436 is outside the ball 411, but inside the outer layer 412. The wall 409 transitions at the inversion fold 432 from the outer layer 412 to an inner layer 438 which has contours that are different from that of the outer layer 412, and extends from the distal orifice 434 to the first end 408. The inner layer 438 comprises a ball 411 having an outer diameter that is less than the outer diameter of the smooth cylindrical section 416. In some embodiments, the outer diameter of the ball 411 is between about 15% and about 95% of the outer diameter of the smooth cylindrical section 416. In some embodiments, the outer diameter of the ball 411 is between about 25% and about 75% of the outer diameter of the smooth cylindrical section 416. In some embodiments, the outer diameter of the ball 411 is between about 33% and about 67% of the outer diameter of the smooth cylindrical section 416. The inner layer 438 extends proximally along an inner tube section 413 to the first end 408. A marker band 417 is attached over the two layers of wall 409 just distal to the ends 408, 410 and within the proximal concavity 415. In some embodiments the marker band 417 is completely within the proximal concavity 415, and in other embodiments the marker band 417 is partially within the proximal concavity 415, and in still other embodiments the marker band 417 is proximal to the proximal concavity 415. The occlusion device 400 is fabricated as an inverted mesh tube 406 having a simple straight elongate configuration, and is subsequently formed into the shape shown in FIGS. 12-13 and heat set into this shape. For example, the occlusion device 400 may be constructed as a single layer mesh tube formed of at least some nickel-titanium alloy filaments, and then inverted on itself. The inverted mesh tube 406 may then be placed into a die or mold comprising one or more pieces, to hold it in the shape of the occlusion device 400. Then, the occlusion device 400 may be subjected to an elevated temperature and then cooled, to lock in the shape, resulting in an occlusion device 400 having at least some superelastic properties. The occlusion device 400 configured to be compressed or compacted within the lumen 148 of a delivery catheter 150 (e.g., microcatheter).

In some embodiments, the occlusion device 400 may comprise some nickel-titanium alloy filaments and some radiopaque elements, comprising platinum, gold, tantalum, or alloys of any of these or other radiopaque materials. In some embodiments, the filaments may comprise drawn filled tubes, such as those comprising a nickel-titanium alloy outer wall and a platinum core. The radiopaque material allows the occlusion device 400 to be visible on radiographs or fluoroscopy. The occlusion device 400 may be configured by controlling how much radiopaque material is used, by either the ratio of radiopaque filaments to non-radiopaque filaments, or by the amount of platinum core in the drawn filled tubes. In this manner, the occlusion device 400 can be selectively fabricated to be sufficiently visible, but not over visible, e.g., overly bright, such that other objects are obscured. In some embodiments, whether any of the filaments comprise radiopaque materials or not, the marker band 417 may be attached adjacent the proximal end 402 by adhesive or epoxy bonding, or swaging, welding or other mechanical attachment. The occlusion device 400 is detachably coupled at a detachable joint 425 (FIG. 12A) at its proximal end 402 to a pusher wire 419 having a distal end 421 and a proximal end 423 (FIG. 12B).

The when the occlusion device 400 is in its expanded configuration (FIGS. 12A-13) the expanded ball 411 provides an axial support that resists the distal end 430 from being able to compact toward the proximal end 402 (or vice versa). Braided aneurysm occlusion devices can often compact after many thousands or millions of heartbeats, and thus thousands or millions of cycles of systolic pressure. The cycles can cause deformation that shortens or otherwise compresses the devices. The ball 411 serves as a central structure that maintains the shape of the outer structure 437 is formed by the outer layer 412.

Figure 14:
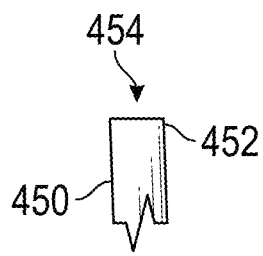
FIGS. 14-18 illustrate the deployment of the occlusion device of FIG. 12A from a delivery catheter.
Figure 15:
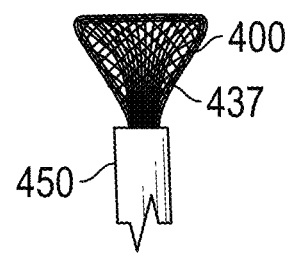
Figure 16:
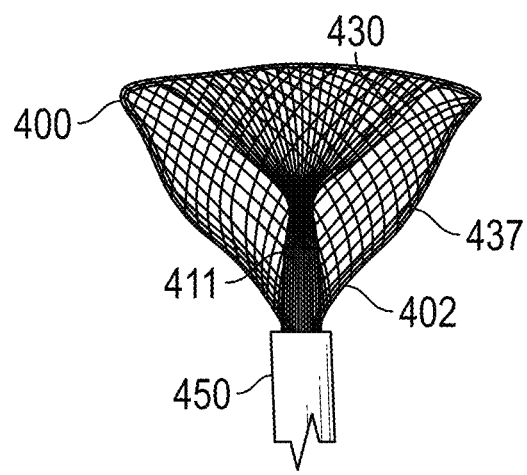
Figure 17:
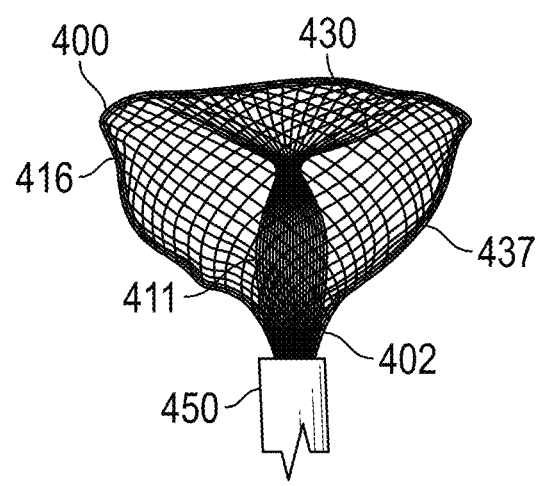
Figure 18:
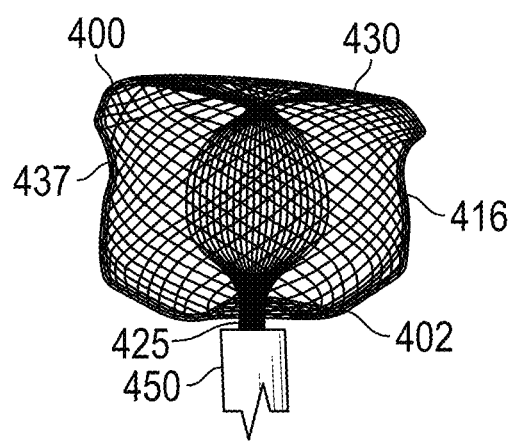

FIGS. 14-18 illustrate the delivery of the occlusion device 400 from its compressed state within the lumen 454 of a delivery catheter 450 to its expanded state. The delivery into an aneurysm would follow the general manner shown in FIGS. 7-10. FIG. 14 illustrates the distal end 452 of the delivery catheter 450. FIG. 15 illustrates the initial delivery of the occlusion device 400 out of the lumen 454 of the delivery catheter 450 by pushing the pusher wire 419 at its proximal end 423 (FIG. 12B). The distal end 430 of the occlusion device 400 is significantly folded up within the mostly compressed outer structure 437. As the pusher wire 419 is further pushed distally, the occlusion device 400 begins to further exit the lumen 454 and expand, as shown in FIG. 16. Much of the distal end 430 begins to unfold from within the outer structure 437. The ball 411 can be seen expanding in FIG. 17, as the pusher wire 419 is pushed and the occlusion device 400 extends further from the lumen 454. The distal end 430 unfolds even more from within the outer structure 437. The smooth cylindrical section 416 begins to take a more definite shape. Finally, as shown in FIG. 18, the fully expanded occlusion device 400 can be seen, without any of the restraints of the lumen 454 of the delivery catheter 450. The rolling, folding or unfolding manner in which the occlusion device 400 compresses and expands allows for a fit within a small diameter delivery catheter. An occlusion device 400 having a 3 mm to 6 mm expanded outer diameter may fit within the inner lumen of a microcatheter having a 0.023 inch inner diameter, or a 0.021 inch inner diameter, or even a 0.017 inch inner diameter.

The proximal end 402 of the occlusion device 400 in its expanded configuration has a significantly large proximal ring-shaped mesh surface 441 (FIG. 12A) that is configured to increase flow diversion and to seat and seal against the proximal portion of the aneurysm such as the portion adjacent the aneurysm neck. Thus, an aneurysm may be fully occluded via biological process in a shorter amount of time than many other devices. The amount of time to full isolation from the blood circulation may be significantly less than one year, and may be as soon as four months, or even as soon as three months.

Figure 19:
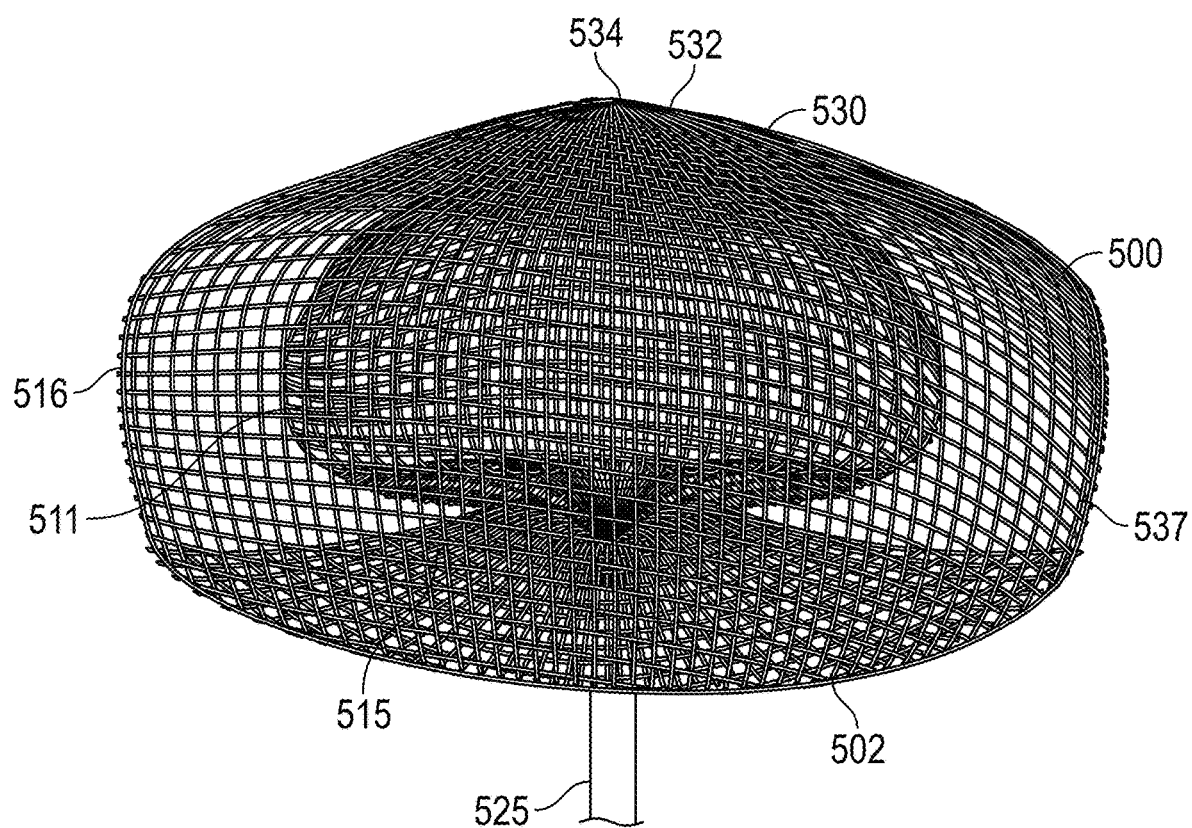
FIG. 19 is a perspective view of an occlusion device, according to an alternative embodiment of the present disclosure.

FIG. 19 illustrates an occlusion device 500 that is similar to the occlusion device 400 of FIG. 12A, however the ball 511 has a mushroom shape. The ball 511 also has a diameter that is significantly greater than 50% of the diameter of the outer structure 537, and is also configured to resist compaction between the distal end 530 and the proximal end 502. The proximal concavity 515 extends for the majority of the diameter of the occlusion device 500. The smooth cylindrical section 516 still includes a significant surface area to seal along the aneurysm wall. Also shown are the inversion fold 532, the distal orifice 534, and the detachable joint 525.

Figure 20:
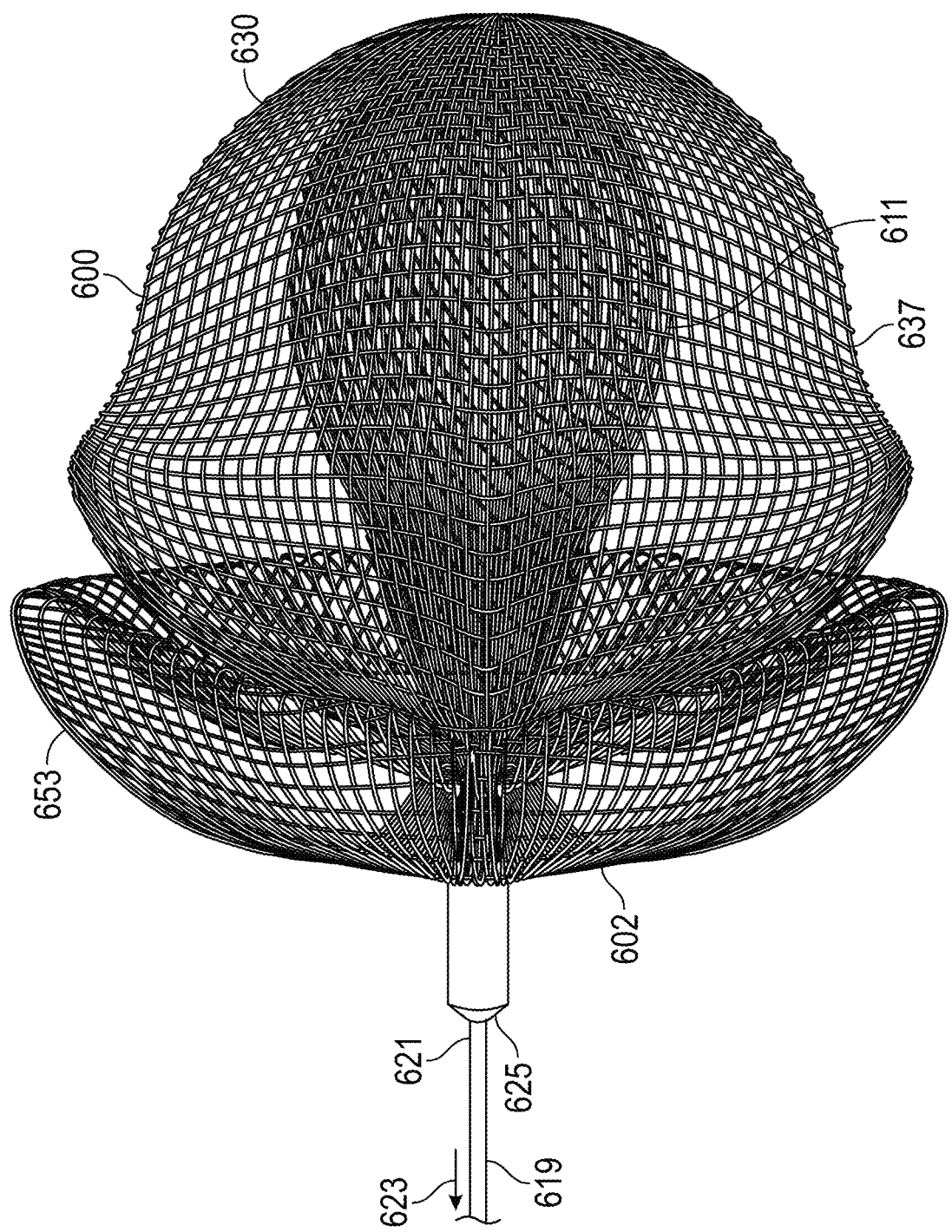
FIG. 20 is a perspective view of an occlusion device, according to an alternative embodiment of the present disclosure.
Figure 21:
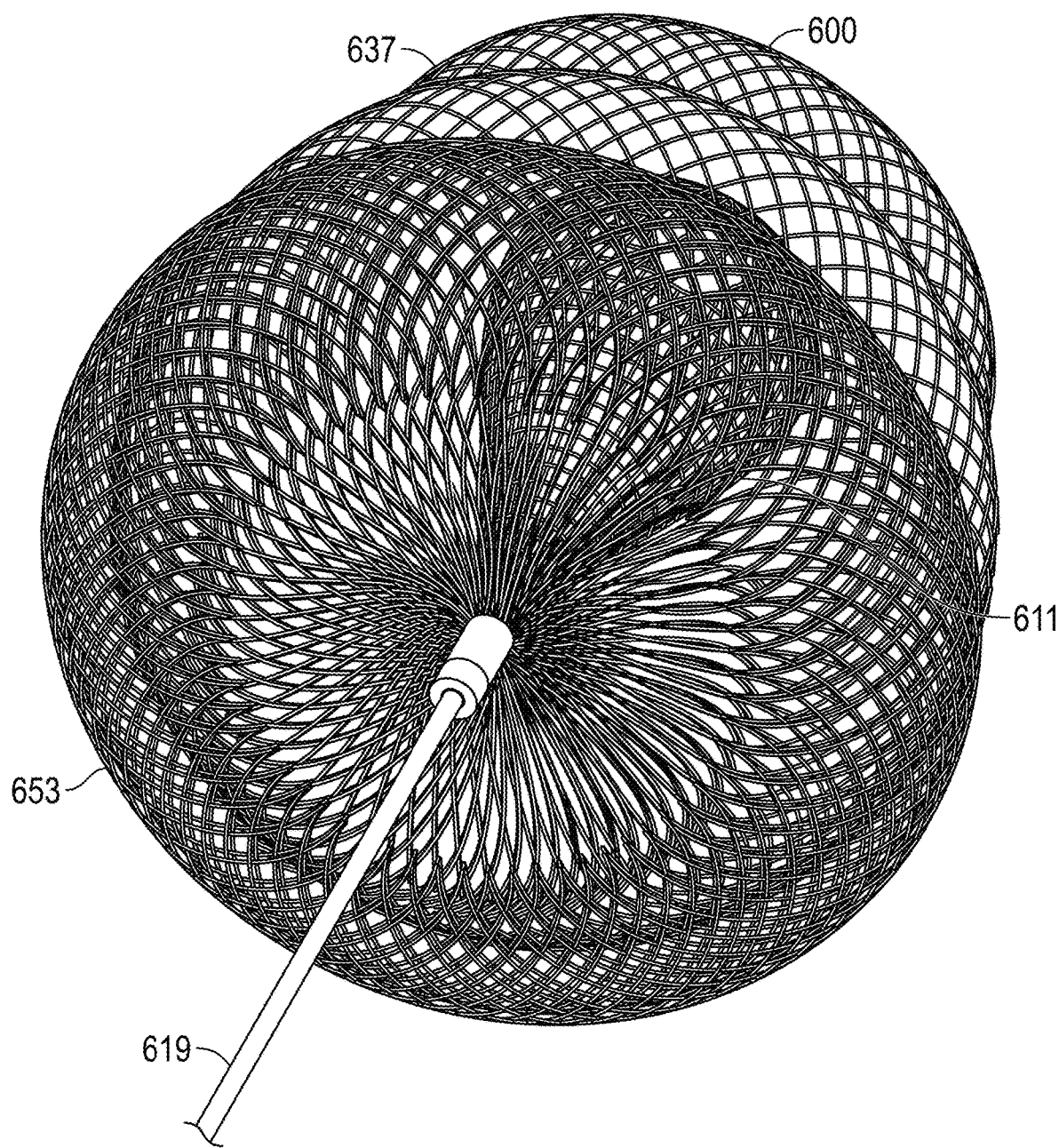
FIG. 21 is another perspective view of the occlusion device of FIG. 20.
Figure 22:
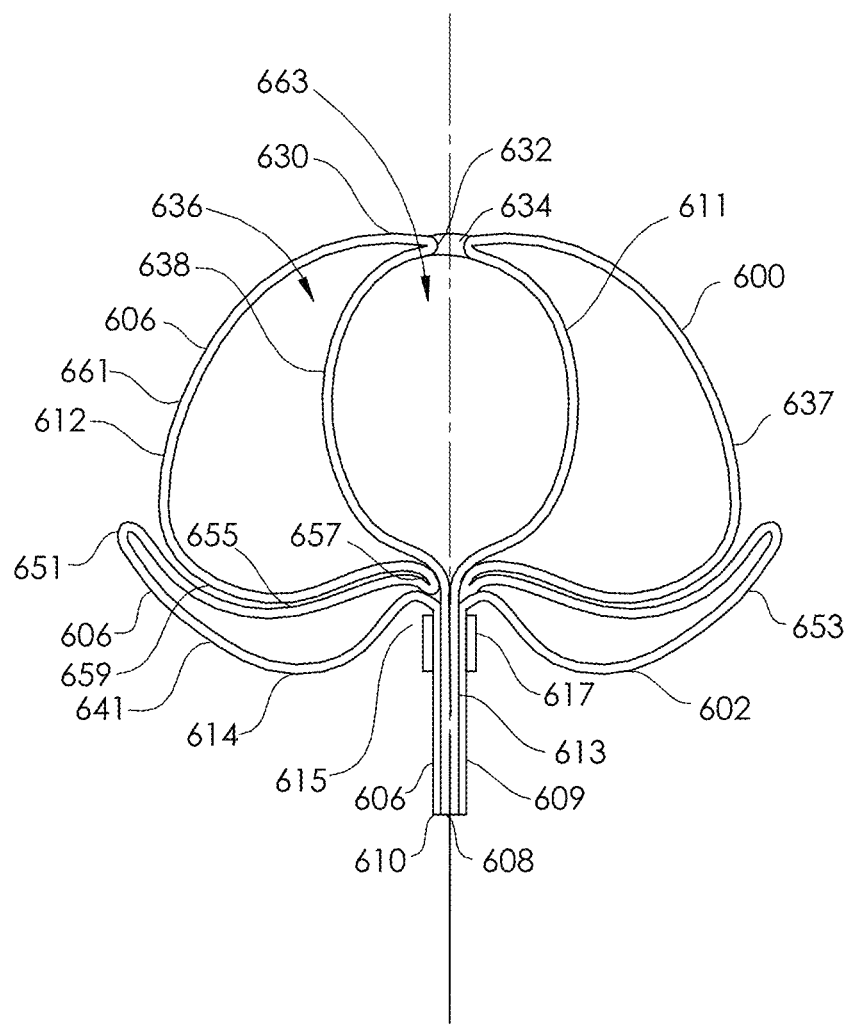
FIG. 22 is a sectional view of the occlusion device of FIG. 20.

FIGS. 20 and 21 illustrate an occlusion device 600 configured for placement within an aneurysm. The occlusion device 600 comprises a proximal end 602 and a distal end 630, and is constructed of a single, continuous dual layer mesh. Turning to FIG. 22, the occlusion device 600 is constructed from an inverted mesh tube 606 having a first end 608, a second end 610, and a wall 609. The inverted mesh tube 606 extends from the second end 610 past a proximal concavity 615 along a convex proximal surface 614 and around an outer fold 651 to form a proximal cover 653. The mesh tube 606 extends inward along a distal cover face 655 and folds toward the center at a center fold 657 An outer layer 612 forms an outer structure 637 and extends along a proximal surface 659, to a side portion 661 and to the distal end 630 of the occlusion device 600. The convex proximal surface 614 of the cover 653 is configured to seal against the aneurysm adjacent the aneurysm wall. The outer diameter of the occlusion device 600 may be between about 3 mm to about 15 mm, or between about 3 mm and about 7 mm. At the distal end 630, the wall 609 is inverted inwardly at an inversion fold 632, which creates a distal orifice 634 and a first internal volume 636 and a second internal volume 663. The second internal volume 663 is inside a ball 611 formed by an inner layer 638 and the first internal volume 636 is outside the ball 611, but inside the outer layer 612. The wall 609 transitions at the inversion fold 632 from the outer layer 612 to the inner layer 638 which has contours that are different from that of the outer layer 612, and extends from the distal orifice 634 to the first end 608. The inner layer 638 comprises the ball 611 having an outer diameter that is less than the outer diameter of the outer structure 637. In some embodiments, the outer diameter of the ball 611 is between about 15% and about 95% of the outer diameter of the outer structure 637. In some embodiments, the outer diameter of the ball 611 is between about 25% and about 75% of the outer diameter of the outer structure 637. In some embodiments, the outer diameter of the ball 611 is between about 33% and about 67% of the outer diameter of the outer structure 637. The inner layer 638 extends proximally along an inner tube section 613 to the first end 608. A marker band 617 is attached over the two layers of wall 609 just distal to the ends 608, 610 and substantially within the proximal concavity 615. The occlusion device 600 is fabricated as an inverted mesh tube 606 having a simple straight elongate configuration, and is subsequently formed into the shape shown in FIGS. 20-22 and heat set into this shape. For example, the occlusion device 600 may be constructed as a single layer mesh tube formed of at least some nickel-titanium alloy filaments, and then inverted on itself. The inverted mesh tube 606 may then be placed into a die or mold comprising one or more pieces, to hold it in the shape of the occlusion device 600. Then, the occlusion device 600 may be subjected to an elevated temperature and then cooled, to lock in the shape, resulting in an occlusion device 600 having at least some superelastic properties. The occlusion device 600 configured to be compressed or compacted within the lumen 148 of a delivery catheter 150 (e.g., microcatheter).

In some embodiments, the occlusion device 600 may comprise some nickel-titanium alloy filaments and some radiopaque elements, comprising platinum, gold, tantalum, or alloys of any of these or other radiopaque materials. In some embodiments, the filaments may comprise drawn filled tubes, such as those comprising a nickel-titanium alloy outer wall and a platinum core. The radiopaque material allows the occlusion device 600 to be visible on radiographs or fluoroscopy. The occlusion device 600 may be configured by controlling how much radiopaque material is used, by either the ratio of radiopaque filaments to non-radiopaque filaments, or by the amount of platinum core in the drawn filled tubes. In this manner, the occlusion device 600 can be selectively fabricated to be sufficiently visible, but not over visible, e.g., overly bright, such that other objects are obscured. In some embodiments, whether any of the filaments comprise radiopaque materials or not, the marker band 617 may be attached adjacent the proximal end 602 by adhesive or epoxy bonding, or swaging, welding or other mechanical attachment. As shown in FIGS. 20-22, the marker band 617 can be configured to partially or completely reside within the proximal concavity 615 when the expanded occlusion device 600 is in its expanded configuration. The occlusion device 600 is detachably coupled at a detachable joint 625 (FIG. 20) at its proximal end 602 to a pusher wire 619 having a distal end 621 and a proximal end 623.

The when the occlusion device 600 is in its expanded configuration (FIGS. 20-22) the expanded ball 611 provides an axial support that resists the distal end 630 from being able to compact toward the proximal end 602 (or vice versa). Braided aneurysm occlusion devices can often compact after many thousands or millions of heartbeats, and thus thousands or millions of cycles of systolic pressure. The cycles can cause deformation that shortens or otherwise compresses the devices. The ball 611 serves as a central structure that maintains the shape of the outer structure 637 is formed by the outer layer 612.

Figure 23:
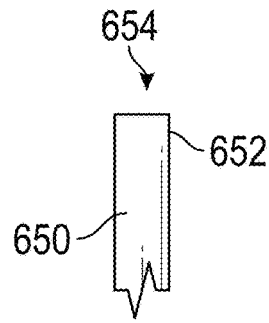
FIGS. 23-28 illustrate the deployment of the occlusion device of FIG. 20 from a delivery catheter.
Figure 24:
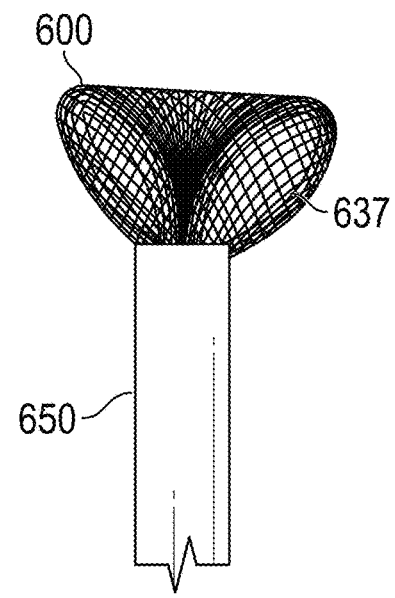
Figure 25:
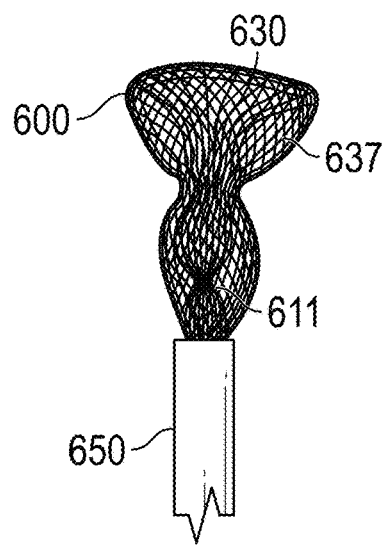
Figure 26:
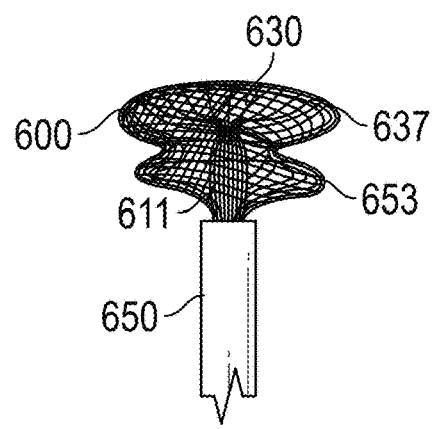
Figure 27:
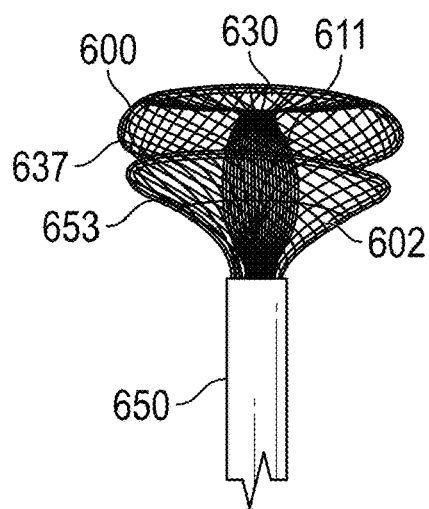
Figure 28:
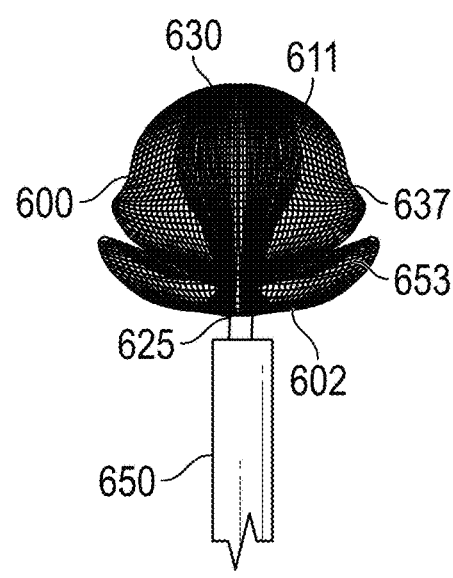

FIGS. 23-28 illustrate the delivery of the occlusion device 600 from its compressed state within the lumen 654 of a delivery catheter 650 to its expanded state. The delivery into an aneurysm would follow the general manner shown in FIGS. 7-10. FIG. 23 illustrates the distal end 652 of the delivery catheter 650. FIG. 24 illustrates the initial delivery of the occlusion device 600 out of the lumen 654 of the delivery catheter 650 by pushing the pusher wire 619 at its proximal end 623. The distal end 630 of the occlusion device 600 is significantly folded up within the mostly compressed outer structure 637. As the pusher wire 619 is further pushed distally, the occlusion device 600 begins to further exit the lumen 654 and expand, as shown in FIG. 25. The ball 611 can be seen expanding in FIG. 26, as the pusher wire 619 is pushed and the occlusion device 600 extends further from the lumen 654. The distal end 630 unfolds more from within the outer structure 637. The outer structure 637 begins to take a more definite shape, and the cover 653 begins to form. In FIG. 27, the cover 653 begins to take a more definite shape, and the ball 611 expands closer to it expanded diameter. Finally, as shown in FIG. 28, the fully expanded occlusion device 600 can be seen, without any of the restraints of the lumen 654 of the delivery catheter 650. The rolling, folding or unfolding manner in which the occlusion device 600 compresses and expands allows for a fit within a small diameter delivery catheter. An occlusion device 600 having a 3 mm to 6 mm expanded outer diameter may fit within the inner lumen of a microcatheter having a 0.023 inch inner diameter, or a 0.021 inch inner diameter, or even a 0.017 inch inner diameter.

The cover 653 at the proximal end 602 of the occlusion device 600 in its expanded configuration has a significantly large proximal ring-shaped mesh surface 641 (FIG. 22) that is configured to increase flow diversion and to seat and seal against the proximal portion of the aneurysm such as the portion adjacent the aneurysm neck. Thus, an aneurysm may be fully occluded via biological process in a shorter amount of time than many other devices. The amount of time to full isolation from the blood circulation may be significantly less than one year, and may be as soon as four months, or even as soon as three months.

Figure 29:
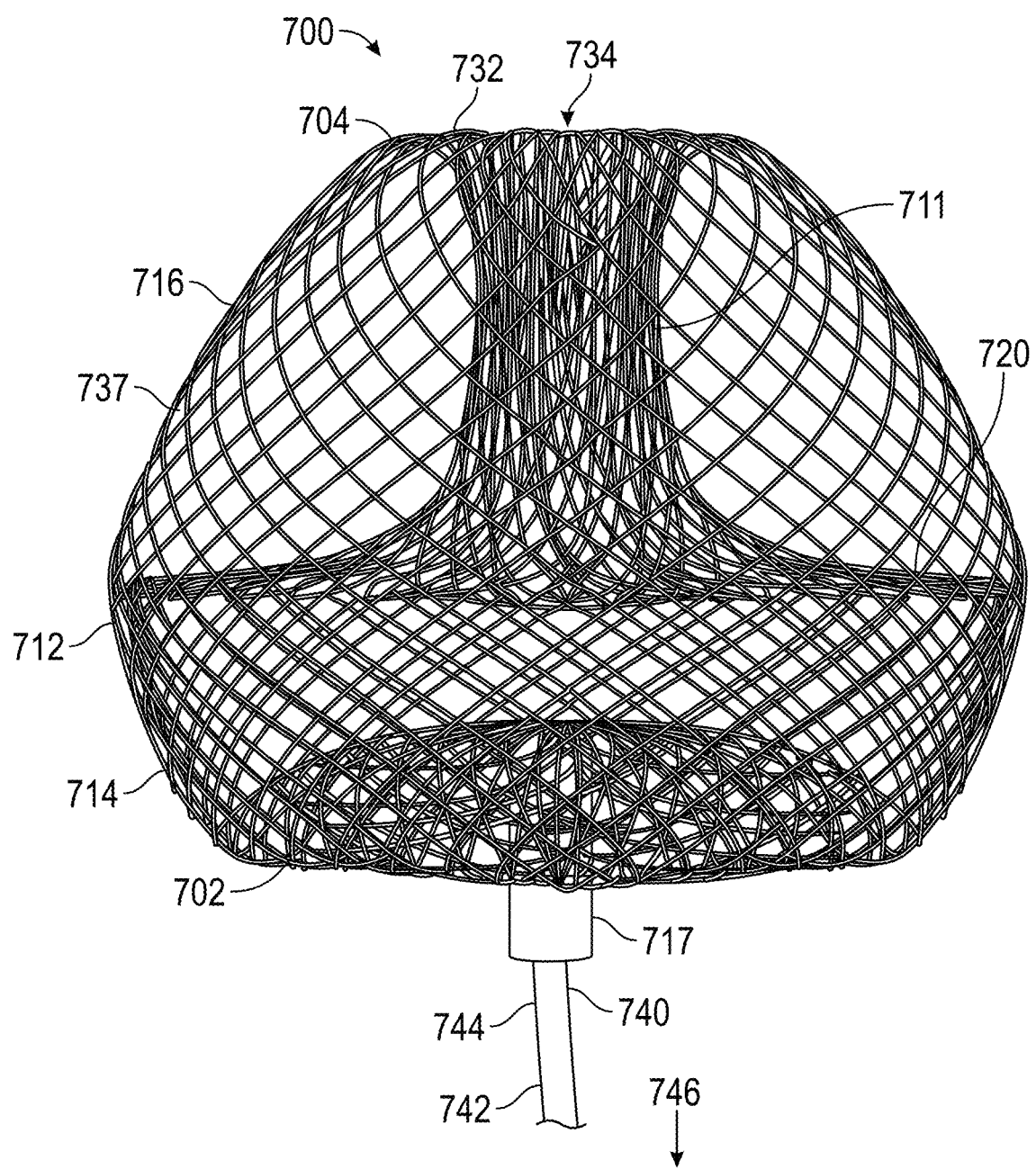
FIG. 29 is a perspective view of an occlusion device, according to an embodiment of the present disclosure.
Figure 30:
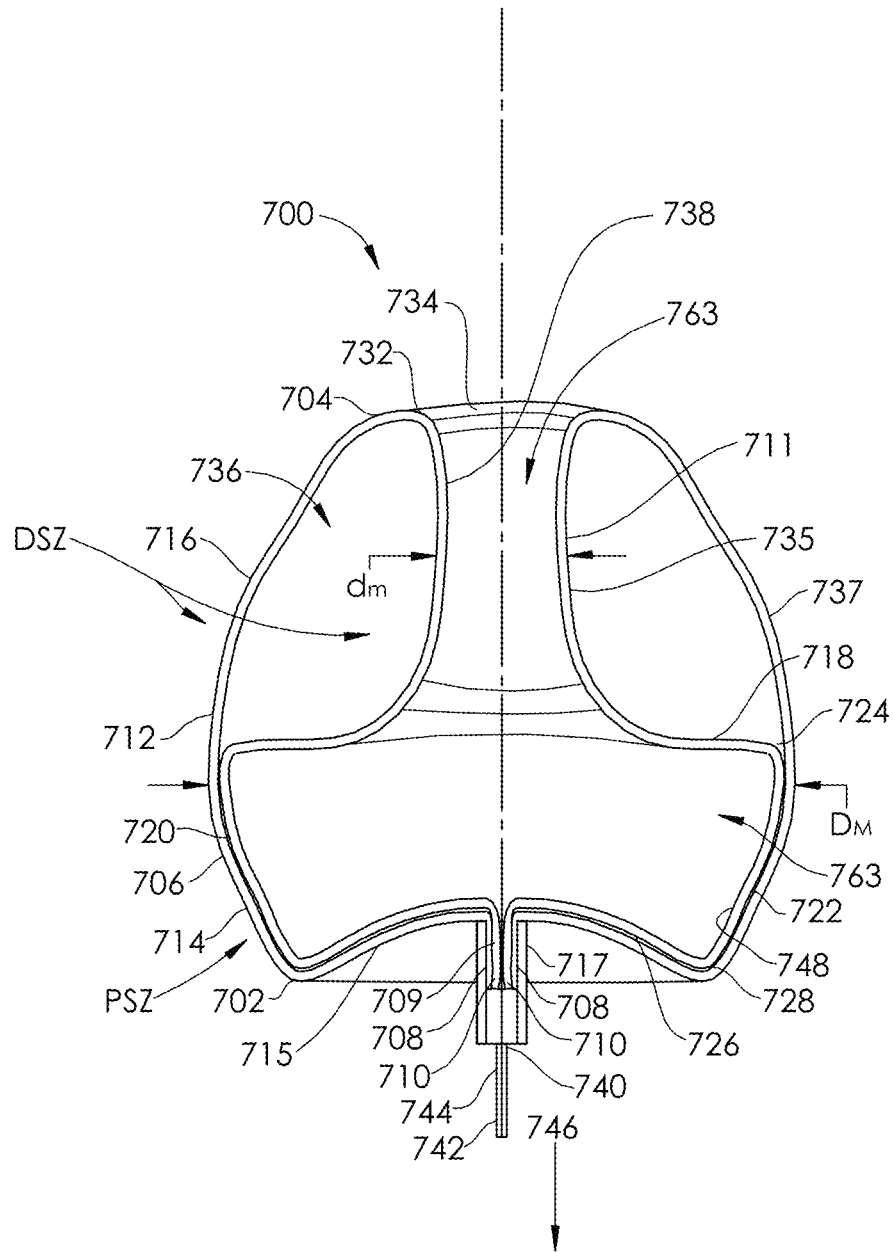
FIG. 30 is a sectional view of the occlusion device of FIG. 29.

FIGS. 29-30 illustrate an occlusion device 700 configured for placement within an aneurysm. The occlusion device 700 comprises a proximal end 702 and a distal end 704, and is constructed of a single, continuous dual layer mesh. The occlusion device 700 is constructed from an inverted mesh tube 706 having a first end 708, a second end 710, and a wall 709. The inverted mesh tube 706 extends from the first end 708 past a proximal concavity 715 along an outer layer 712 comprising a globular contour 737 having a proximal outer surface 714 and a distal outer surface 716. The proximal outer surface 714 is configured to seal against the aneurysm adjacent the aneurysm wall. The outer diameter of the occlusion device 700 may be between about 3 mm to about 15 mm, or between about 3 mm and about 7 mm. At the distal end 704, the wall 709 is inverted inwardly at an inversion fold 732, which creates a distal orifice 734 and a first internal volume 736 and a second internal volume 763. The inversion fold also divides the wall 709 into the outer layer 712 and an inner layer 738. The second internal volume 763 is inside a column 711 formed by the inner layer 738, and the first internal volume 736 is outside the column 711, but inside the outer layer 712. The inner layer 738 has contours that are different from that of the outer layer 712, and extends from the distal orifice 734 to the second end 710. The column 711 extends proximally from the inversion fold 732. The inner layer 738 comprises the column 711 which has an outer diameter that is less than the outer diameter of the globular contour 737. The column 711 includes a circumferentially-extending concavity 735, and thus comprises a hyperboloid. In some embodiments, the column 711 has a minimum diameter $d_m$ that is between about 5% and about 50% of the maximum diameter $D_M$ of the globular contour 737. In some embodiments, the column 711 has a minimum diameter $d_m$ that is between about 5% and about 25% of the maximum diameter $D_M$ of the globular contour 737.

The inner layer 738 extends along the column 711, and then forms an inner cover 720 by extending outward radially along an inner cover distal face 718 to an inner cover outer face 722. The distal face 718 transitions to the outer face 722 at a maximum diameter portion 724. The outer face 722 tapers to the maximum diameter portion 724, from proximal to distal. However, in alternative embodiments, the outer face 722 may have no significant taper, or may even taper in the opposite manner, with the maximum diameter being at or near the proximal end. The inner cover 720 then transitions to an inner cover proximal face 726 at a proximal end 728. The proximal face 726 is immediately adjacent the proximal concavity 715 of the outer layer 712, thus creating two layers at the neck portion of the aneurysm, when the occlusion device 700 is deployed therein. The outer face 722 is immediately adjacent the proximal outer surface 714 of the outer layer 712, thus creating two layers adjacent the neck portion of the aneurysm. The dual layers at and adjacent the neck of the aneurysm serve to increase the overall density of the mesh (e.g., the total number of crossings, or the total pics per inch or pics per mm), to thus aid in the disruption or stagnation of flow at the neck. In some embodiments, the column 711 has a minimum diameter $d_m$ that is between about 5% and about 50% of the diameter of the maximum diameter portion 724 of the inner cover 720. In some embodiments, the column 711 has a minimum diameter $d_m$ that is between about 5% and about 25% of the diameter of the maximum diameter portion 724 of the inner cover 720. In some embodiments, the column 711 has a length (proximal to distal, along a longitudinal axis) that is between about 30% and about 150% a length (proximal to distal, along a longitudinal axis) of the inner cover 720. In some embodiments, the column 711 has a length (proximal to distal, along a longitudinal axis) that is between about 50% and about 90% a length (proximal to distal, along a longitudinal axis) of the inner cover 720. In some embodiments, the column 711 has a length (proximal to distal, along a longitudinal axis) that is between about 50% and about 70% a length (proximal to distal, along a longitudinal axis) of the inner cover 720. In some embodiments, the column 711 has a length (proximal to distal, along a longitudinal axis) that is between about 20% and about 90% a total length of the occlusion device between the proximal end 702 and the distal end 704.

The inner layer 738 thus extends from the inversion fold 732, through the column 711, and the entirety of the inner cover 720, to the second end 710. A marker band 717 is attached over the two layers of wall 709 just distal to the ends 708, 710. The marker band 717 may comprise a radiopaque material such as platinum, platinum/iridium, or tantalum, for viewing on x-ray or fluoroscopy, as may any of the marker bands described herein. The occlusion device 700 is fabricated as an inverted mesh tube 706 having a simple straight elongate configuration, and is subsequently formed into the shape shown in FIGS. 29-30 and heat set into this shape, to create an expanded state. For example, the occlusion device 700 may be constructed as a single layer mesh tube formed of at least some nickel-titanium alloy filaments, and then inverted on itself. The inverted mesh tube 706 may then be placed into a die or mold comprising one or more pieces, to hold it in the shape of the occlusion device 700. Then, the occlusion device 700 may be subjected to an elevated temperature and then cooled, to lock in the shape, resulting in an occlusion device 700 having at least some superelastic properties. The occlusion device 700 configured to be compressed or compacted within the lumen 654 of a delivery catheter 650 (e.g., microcatheter), having a distal end 652 (FIGS. 32-36).

In the expanded state of the occlusion device 700, the column 711 serves as an internal support to reduce the compressibility of the outer layer 712, and thus to maintain the shape of the globular contour 737, even throughout long-term implantation within an aneurysm. The column 711, with its larger density of crossings/pics (e.g., smaller average pore size) provides a distal stagnation or flow disruption nidus. The column 711 has a significantly smaller pore size than the outer layer 712 when the occlusion device 700 is in its expanded state. The column 711 also has a significantly smaller pore size than the inner cover 720 when the occlusion device 700 is in its expanded state. In some pre-clinical studies performed by the inventors, an almost-immediate thrombosis was achieved in experimental aneurysms in animals. The thrombosis progressed in a top-down manner, beginning in the distal region of the occlusion device 700 that includes the column 720. The efficiency of the flow stagnation or disruption in the distal area of the occlusion device is aided by the complexity provided by the inner column contour, the outer layer contour, and the density of the crossings/pics in the column. The column 711 additionally is able to apply an axial force to maintain the inner cover 720 and proximal outer surface 714 against the neck of the aneurysm. Thus, the occlusion device 700 includes a distal stagnation zone DSZ and a proximal stagnation zone PSZ.

Figure 37:
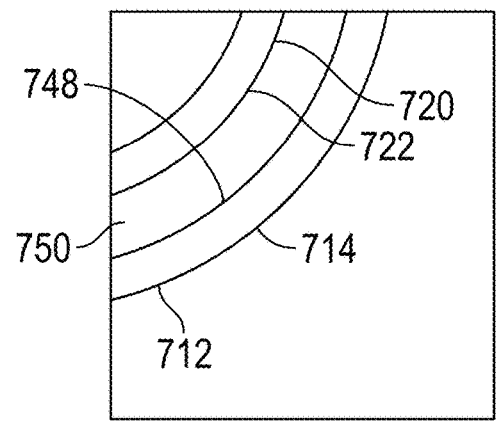
FIG. 37 illustrates is a sectional view of an alternative occlusion device configuration according to an embodiment of the present disclosure.

In some embodiments, when the occlusion device 700 is in its expanded state, the outer face 722 of the inner cover 720 may provide an outward radial stress on the outer layer 712 at an inner portion 748 opposite the proximal outer surface 714, thus serving to increase the overall radial expansion and/or radial gripping to the aneurysm wall. In other embodiments, there may be an annular space 750 between the outer face 722 of the inner cover 720 and the inner portion 748 (FIG. 37). The annular space 750 may serve multiple purposes. The annular space 750 may allow for some freedom-of-movement between the outer layer 712 and the inner cover 720. The annular space 750 may also, or alternatively, provide an additional stagnation layer between the outer layer 712 and the inner cover 720, to increase flow stagnation or disruption. The word "globular" as used herein does not strictly limit to a sphere. Any shape having somewhat smooth and/or rounded contours and which displaces a space having a relatively low surface-to-volume ratio may be considered "globular" for purposes herein. For example, the outer extents of the occlusion device 700 as shown in FIG. 29 and as shown in FIG. 30 are considered globular.

The occlusion device 700 is detachably coupled at a detachable joint 740 at its proximal end 702 to a pusher wire 742 having a distal end 744 and a proximal end 746. The detachable joint 740 may comprise one of a number of detachment systems, including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems. In any of the embodiments disclosed herein, alternative detachable joint may be employed, such as the detachable joints disclosed in U.S. Pat. No. 11,058,431, issued Jul. 13, 2021, and entitled "Systems and Methods for Treating Aneurysms" and in U.S. Pat. No. 10,856,880, issued Dec. 8, 2020, and entitled "Systems and Methods for Treating Aneurysms."

Figure 32:
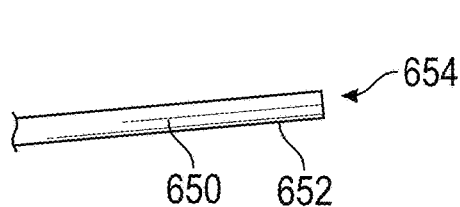
FIGS. 32-36 illustrate the deployment of the occlusion device of FIG. 29 from a delivery catheter.
Figure 33:
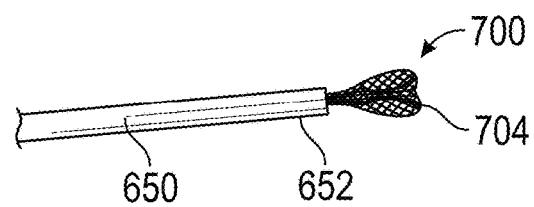
Figure 34:
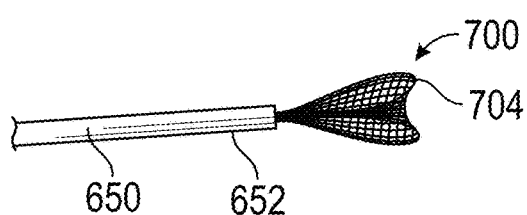
Figure 35:
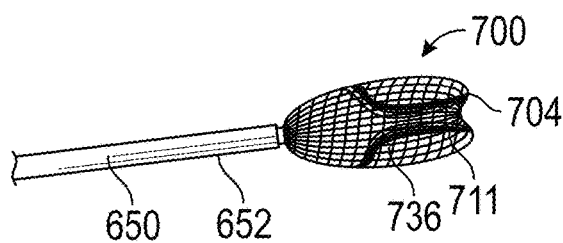
Figure 36:
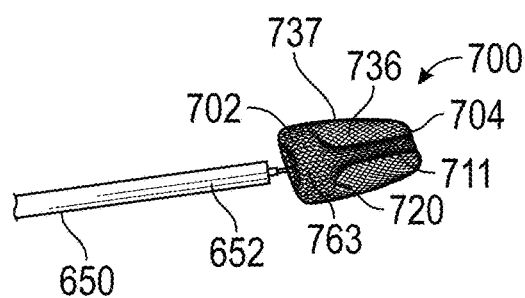

FIGS. 32-36 illustrate the delivery of the occlusion device 700 from its compressed state within the lumen 654 of a delivery catheter 650 to its expanded state. FIG. 32 illustrates the distal end 652 of the delivery catheter 650. FIG. 33 illustrates the initial delivery of the occlusion device 700 out of the lumen 654 of the delivery catheter 650 by pushing the pusher wire 742 at its proximal end 746. The majority of the occlusion device 700 is still significantly compressed. As the pusher wire 742 is further pushed distally, the occlusion device 700 begins to further exit the lumen 654 and expand, as shown in FIG. 34. The column 711 can be seen expanding in FIG. 35, as the pusher wire 742 is pushed and the occlusion device 700 extends further from the lumen 654. The globular contour 737 of the outer layer 712 begins to take a more definite shape, and the inner cover 720 significantly beings taking its shape. In FIG. 36, the inner cover 720, the globular contour 737, and the column 711 each take their expanded shapes of the occlusion device 700 in its expanded state, without any of the restraints of the lumen 654 of the delivery catheter 650. An occlusion device 700 having a 3 mm to 6 mm expanded outer diameter may fit within the inner lumen of a microcatheter having a 0.023 inch inner diameter, or a 0.021 inch inner diameter, or even a 0.017 inch inner diameter.

Figure 31:
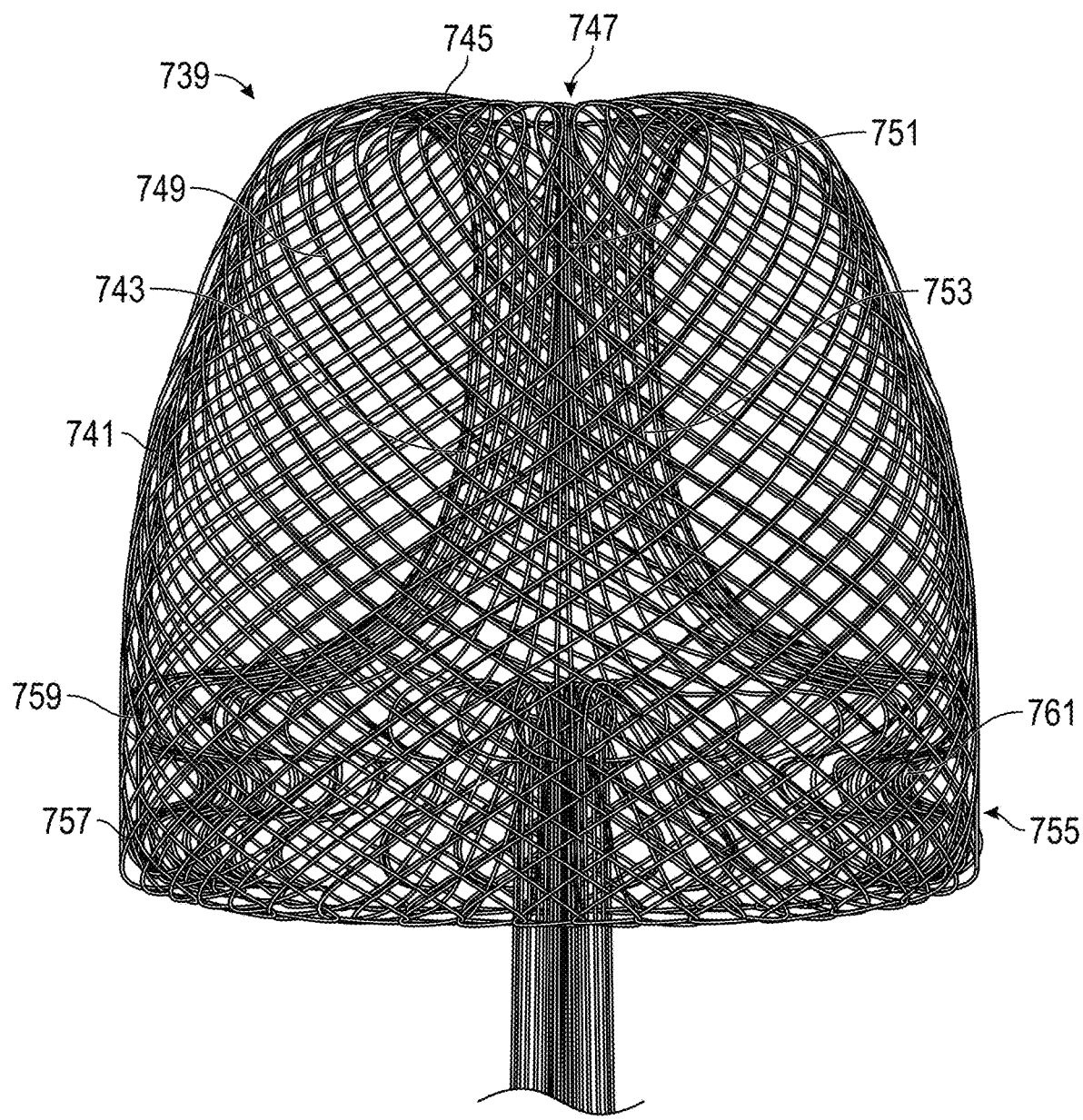
FIG. 31 is a perspective view of an occlusion device, according to an embodiment of the present disclosure.

FIG. 31 illustrates an alternative embodiment of an occlusion device 739, similar to the device 700 of FIGS. 29-30, and also comprising an inverted mesh tube having an outer layer 741 and an inner layer 743 which transition at a transition fold 745. The transition fold 745 forms a distal orifice 747, and the shapes of the outer layer 741 and inner layer 743 form a first internal volume 749 and a second internal volume 751. In the occlusion device 739 of FIG. 31, the inner layer 743 forms a distal column 753, and at a proximal portion 755, a first proximal ring 757 and a second distal ring 759. A circumferentially extending concavity 761 separates the first proximal ring 757 and the second distal ring 759. The presence of both rings 757, 759 at the proximal portion 755 of the occlusion device 739 increases the number of crossings in the braid, and provides a significant stagnation zone. The stacking of the rings 757, 759 and the column 753 together create additional support against axial compaction of the occlusion device 739, e.g., even after many blood pressure cycles.

Figure 38:
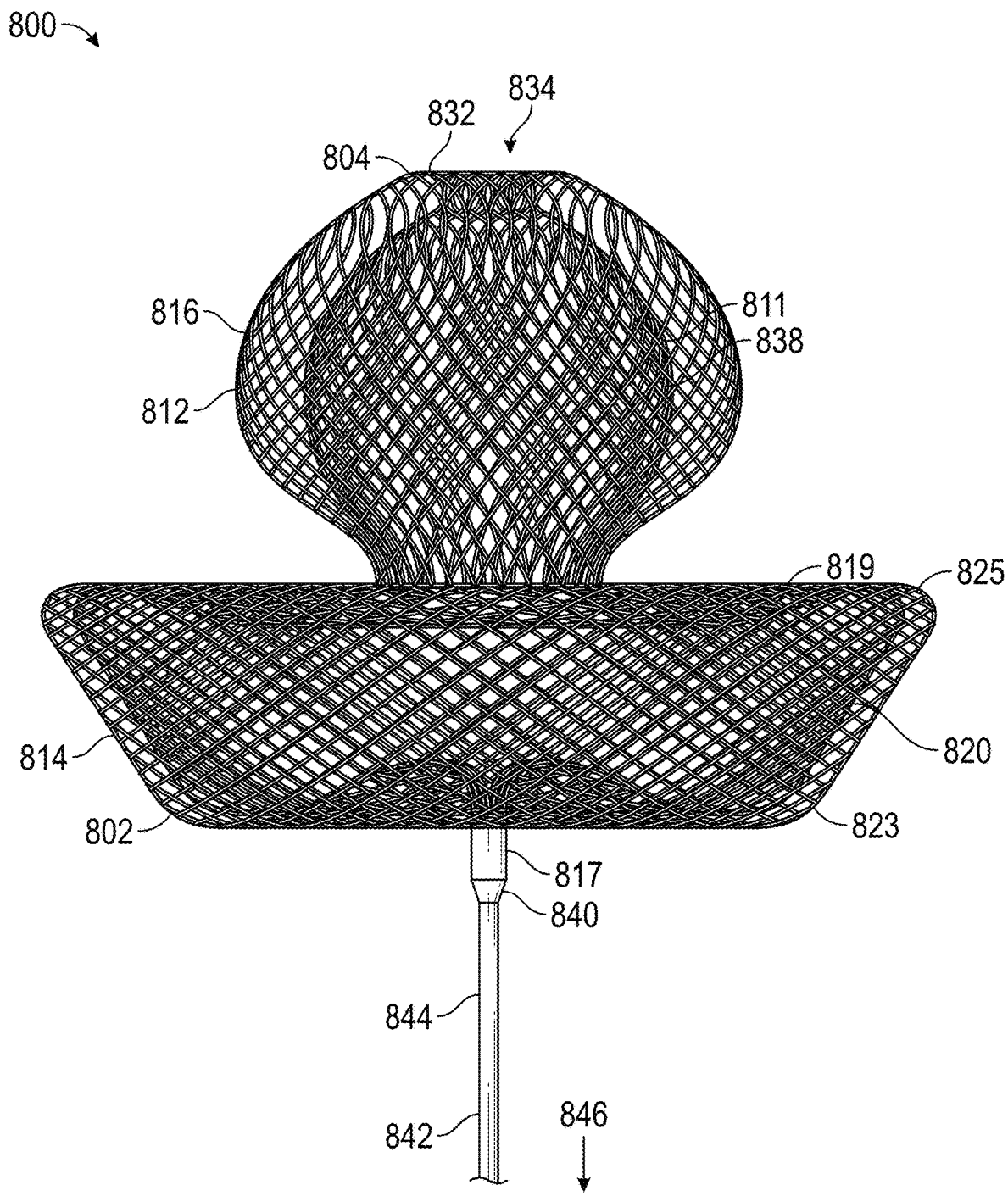
FIG. 38 is a perspective view of an occlusion device, according to an embodiment of the present disclosure.
Figure 39:
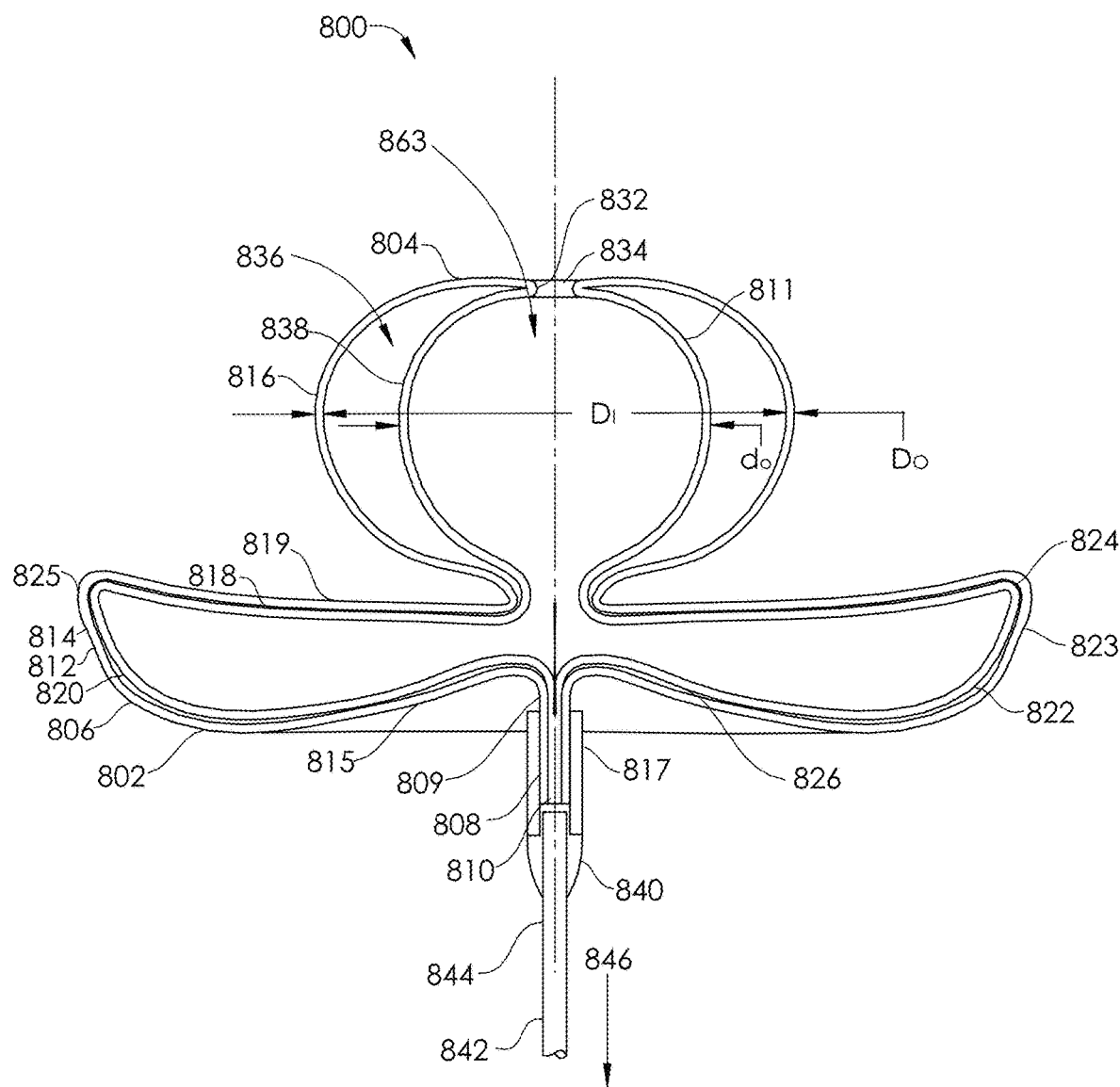
FIG. 39 is a sectional view of the occlusion device of FIG. 38.

FIGS. 38-39 illustrate an occlusion device 800 configured for placement within an aneurysm. The occlusion device 800 comprises a proximal end 802 and a distal end 804, and is constructed of a single, continuous dual layer mesh. The occlusion device 800 is constructed from an inverted mesh tube 806 having a first end 808, a second end 810, and a wall 809. The inverted mesh tube 806 extends from the first end 808 past a proximal concavity 815 along an outer layer 812 which forms a proximal outer cover 814 and a distal outer ball 816. The proximal outer cover 814 is configured to seal against the aneurysm adjacent the aneurysm wall. The outer diameter of the proximal outer cover 814 of the occlusion device 800 may be between about 3 mm to about 15 mm, or between about 3 mm and about 7 mm. At the distal end 804, the wall 809 is inverted inwardly at an inversion fold 832, which creates a distal orifice 834 and a first internal volume 836 and a second internal volume 863. The inversion fold also divides the wall 809 into the outer layer 812 and an inner layer 838. The second internal volume 863 is inside a distal inner ball 811 formed by the inner layer 838, and the first internal volume 836 is outside the distal inner ball 811, but inside the distal outer ball 816. The inner layer 838 has contours that are similar to that of the outer layer 812, and extends from the distal orifice 834 to the second end 810. However, the inner layer 838 does not touch the outer layer 812 throughout its track. The outer diameter $d_o$ of the distal inner ball 811 is less than the inner diameter $D_I$ of the distal outer ball 816, thus providing the annular, shell-like space that defines the first internal volume 836. The distal inner ball 811 extends proximally from the inversion fold 832. In some embodiments, the distal inner ball 811 has an outer diameter $d_o$ that is between about 40% and about 98% of the outer diameter $D_O$ of the distal outer ball 816. In some embodiments, the distal inner ball 811 has an outer diameter $d_o$ that is between about 50% and about 90% of the outer diameter $D_O$ of the distal outer ball 816. In some embodiments, the distal inner ball 811 has an outer diameter $d_o$ that is between about 60% and about 80% of the outer diameter $D_O$ of the distal outer ball 816.

The inner layer 838 extends along the distal inner ball 811, and then forms an inner cover 820 by extending outward radially along an inner cover distal face 818 to an inner cover outer face 822. The distal face 818 transitions to the outer face 822 at a maximum diameter portion 824. The proximal outer cover 814 has a matching distal face 819, outer face 823, and maximum diameter portion 825. The outer face 822 of the inner cover 820 tapers to the maximum diameter portion 824, from proximal to distal. However, in alternative embodiments, the outer face 822 may have no significant taper, or may even taper in the opposite manner, with the maximum diameter being at or near the proximal end. The same is possible with the proximal outer cover 814. In some embodiments, the proximal outer cover 814 and the inner cover 820 may purposely be non-matching. In other words, the inner cover 820 may have its maximum diameter portion 824 proximally and taper thereto, and the proximal outer cover 814 may have its maximum diameter portion distally and taper thereto. The inner cover 820 then transitions to an inner cover proximal face 826 at a proximal end 802. The proximal face 826 is immediately adjacent the proximal concavity 815 of the outer layer 812, thus creating two layers at the neck portion of the aneurysm, when the occlusion device 800 is deployed therein. The outer face 822 and the outer face 823 create two layers adjacent the neck portion of the aneurysm. The dual layers at and adjacent the neck of the aneurysm serve to increase the overall density of the mesh (e.g., the total number of crossings, or the total pics per inch or pics per mm), to thus aid in the disruption or stagnation of flow at the neck. In some embodiments, the distal inner ball 811 has a length (proximal to distal, along a longitudinal axis) that is between about 20% and about 90% a total length of the occlusion device between the proximal end 802 and the distal end 804.

The inner layer 838 thus extends from the inversion fold 832, through the distal inner ball 811, and the entirety of the inner cover 820, to the second end 810. A marker band 817 is attached over the two layers of wall 809 just distal to the ends 808, 810. The marker band 817 may comprise a radiopaque material such as platinum, platinum/iridium, or tantalum, for viewing on x-ray or fluoroscopy. The occlusion device 800 is fabricated as an inverted mesh tube 806 having a simple straight elongate configuration, and is subsequently formed into the shape shown in FIGS. 38-39 and heat set into this shape, to create an expanded state. For example, the occlusion device 800 may be constructed as a single layer mesh tube formed of at least some nickel-titanium alloy filaments, and then inverted on itself. The inverted mesh tube 806 may then be placed into a die or mold comprising one or more pieces, to hold it in the shape of the occlusion device 800. Then, the occlusion device 800 may be subjected to an elevated temperature and then cooled, to lock in the shape, resulting in an occlusion device 800 having at least some superelastic properties. The occlusion device 800 configured to be compressed or compacted within the lumen 654 of a delivery catheter 650 (e.g., microcatheter), having a distal end 652.

In the expanded state of the occlusion device 800, the distal inner ball 811 serves as an internal support to reduce the compressibility of the outer layer 812, and thus to maintain the shape of the distal outer ball 816, even throughout long-term implantation within an aneurysm. The distal inner ball 811, may comprise a larger density of crossings/pics (e.g., smaller average pore size) than the distal outer ball 816, to help increase distal stagnation or flow disruption nidus. The distal inner ball 811 may have a significantly smaller pore size than the distal outer ball 816 when the occlusion device 800 is in its expanded state. The distal inner ball 811 may also have a significantly smaller pore size than the proximal outer cover 814 and/or the inner cover 820 when the occlusion device 800 is in its expanded state. Thus, the occlusion device 800 may include a distal stagnation zone (balls 811, 816) and a proximal stagnation zone (covers 814, 820).

In some embodiments, when the occlusion device 800 is in its expanded state, the inner cover 820 may provide an outward radial stress on the distal outer cover 814, somewhat similar to what was previously described in relation to the occlusion device 700, thus serving to increase the overall radial expansion and/or radial gripping to the aneurysm wall. In other embodiments, there may be an annular space between the inner cover 820 and the distal outer cover 814, as described in relation to FIG. 37. The ball shape of either ball 811, 816 may be "globular" as broadly defined herein.

The occlusion device 800 is detachably coupled at a detachable joint 840 at its proximal end 802 to a pusher wire 842 having a distal end 844 and a proximal end 846. The detachable joint 840 may comprise one of a number of detachment systems, including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems. In any of the embodiments disclosed herein, alternative detachable joint may be employed, such as the detachable joints disclosed in U.S. Pat. No. 11,058,431, issued Jul. 13, 2021, and entitled "Systems and Methods for Treating Aneurysms" and in U.S. Pat. No. 10,856,880, issued Dec. 8, 2020, and entitled "Systems and Methods for Treating Aneurysms."

Figure 45:
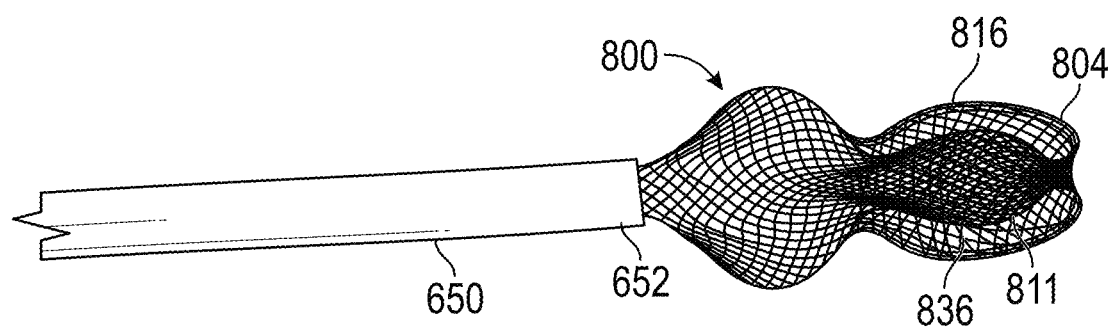
Figure 46:
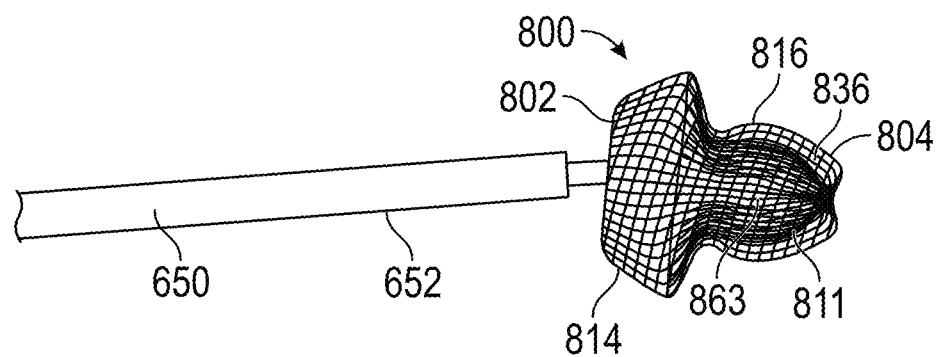

FIGS. 40-46 illustrate the delivery of the occlusion device 800 from its compressed state within the lumen 654 of a delivery catheter 650 to its expanded state. FIG. 40 illustrates the distal end 652 of the delivery catheter 650. FIG. 41 illustrates the initial delivery of the occlusion device 800 out of the lumen 654 of the delivery catheter 650 by pushing the pusher wire 842 at its proximal end 846. The majority of the occlusion device 800 is still significantly compressed. As the pusher wire 842 is further pushed distally, the occlusion device 800 begins to further exit the lumen 654 and expand, as shown in FIG. 42. The distal inner ball 811 can be seen expanding in FIG. 42 and FIG. 43, as the pusher wire 842 is pushed and the occlusion device 800 extends further from the lumen 654. In FIG. 44, the outer layer 812 begins to take a more definite shape, although the proximal outer cover 814 is still exiting the lumen 654. In FIG. 45, the occlusion device 800 is extended a bit more. In FIG. 46, the proximal outer cover 814 and the two balls 811, 816 each take their expanded shapes of the occlusion device 800 in its expanded state, without any of the restraints of the lumen 654 of the delivery catheter 650. An occlusion device 800 having a 3 mm to 6 mm expanded outer diameter may fit within the inner lumen of a microcatheter having a 0.023 inch inner diameter, or a 0.021 inch inner diameter, or even a 0.017 inch inner diameter.

Figure 47:
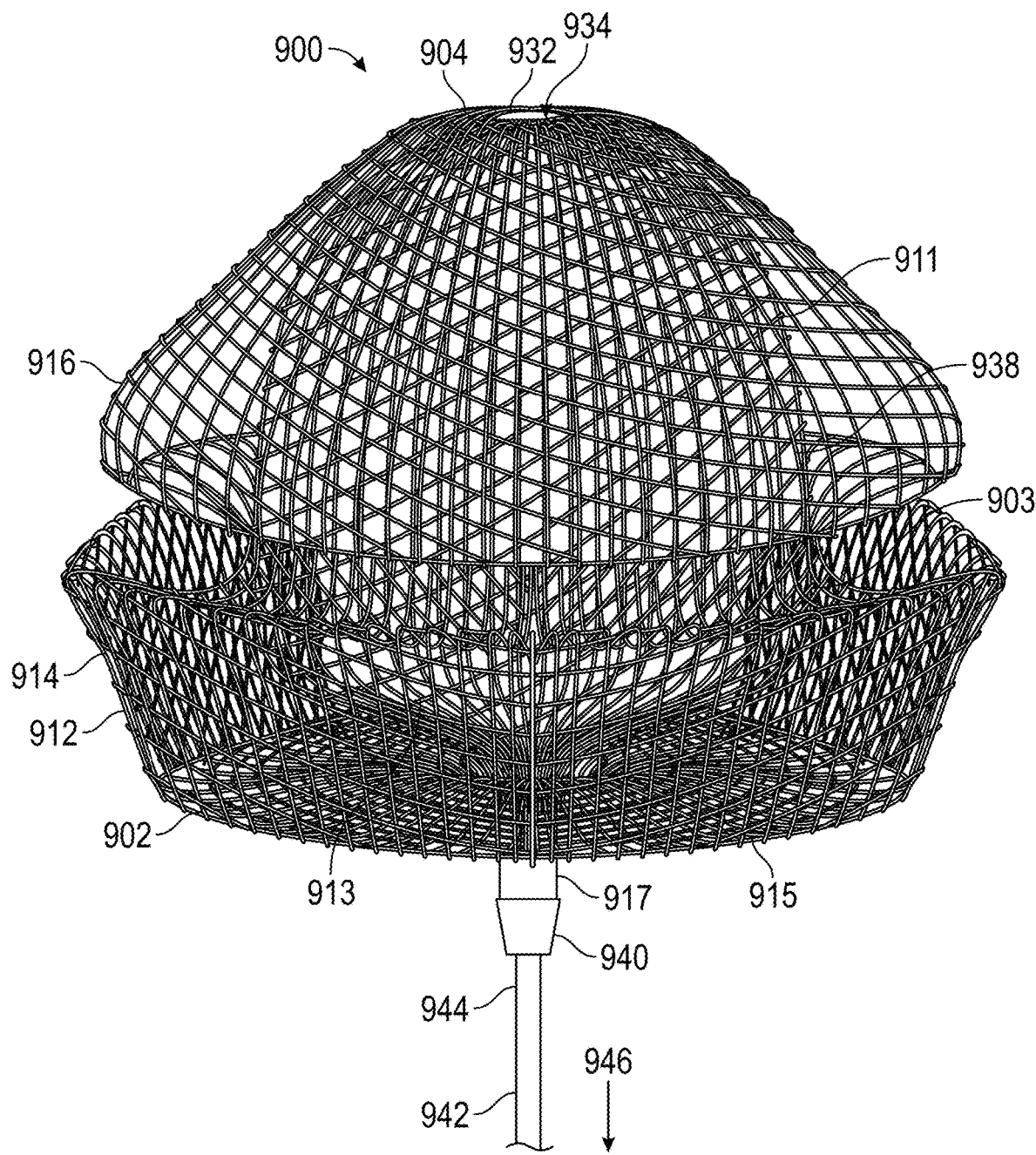
FIG. 47 is a perspective view of an occlusion device, according to an embodiment of the present disclosure.
Figure 48:
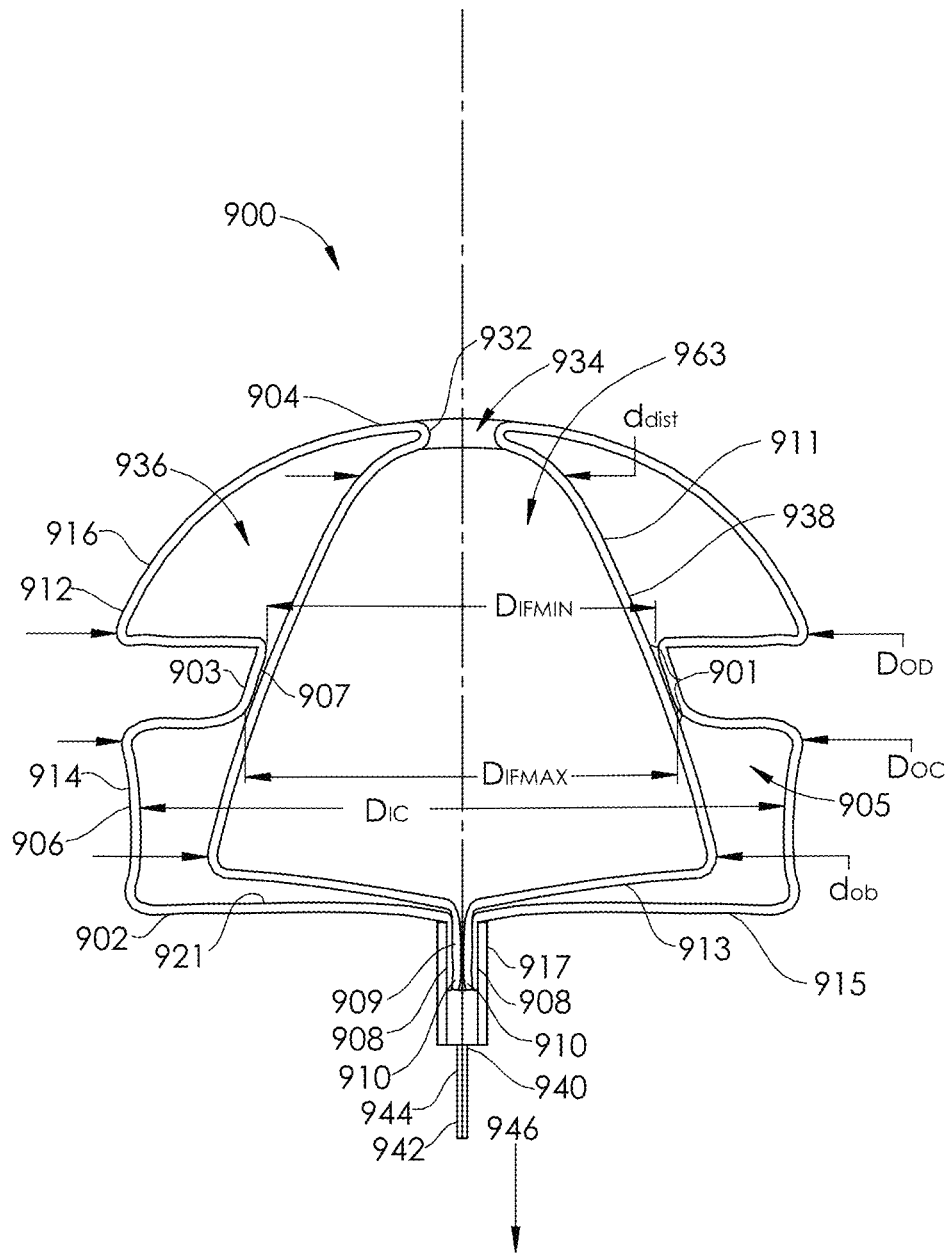
FIG. 48 is a sectional view of the occlusion device of FIG. 47.
Figure 54:
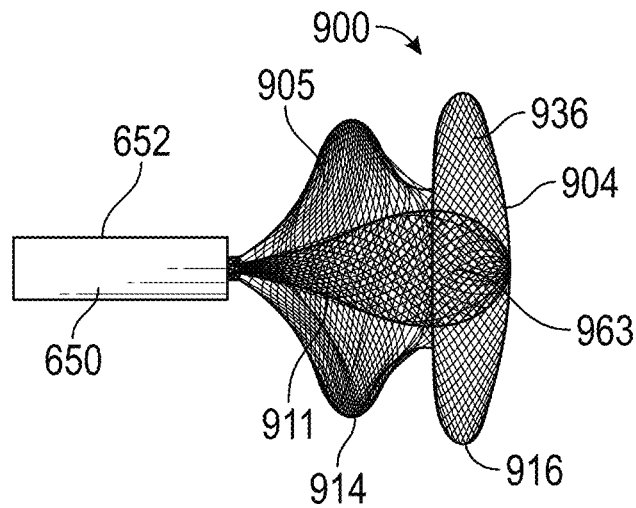
Figure 55:
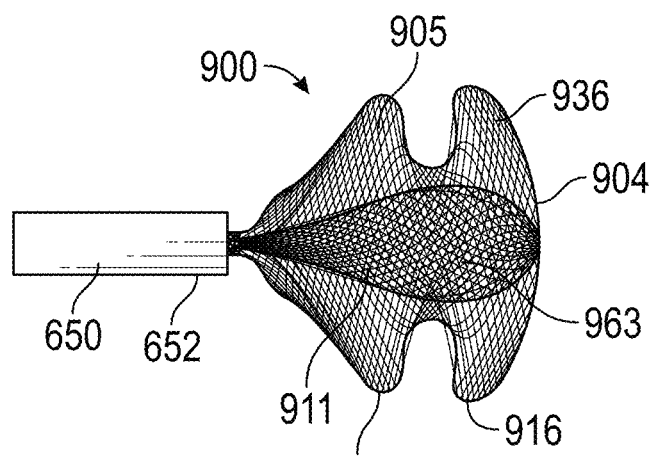

FIGS. 47-48 illustrate an occlusion device 900 configured for placement within an aneurysm. The occlusion device 900 comprises a proximal end 902 and a distal end 904, and is constructed of a single, continuous dual layer mesh. The occlusion device 900 is constructed from an inverted mesh tube 906 having a first end 908, a second end 910, and a wall 909. The inverted mesh tube 906 extends from the first end 908 past a proximal face 915 along an outer layer 912 which forms a proximal outer cover 914 and a distal outer dome 916. The proximal outer cover 914 is configured to seal against the aneurysm adjacent the aneurysm wall. The outer diameter of the proximal outer cover 914 of the occlusion device 900 may be between about 3 mm to about 15 mm, or between about 3 mm and about 7 mm. The distal outer dome 916 may comprise a hemisphere or a partial portion of a sphere, or a partial portion of any globular shape, as defined broadly herein. At the distal end 904, the wall 909 is inverted inwardly at an inversion fold 932, which creates a distal orifice 934 and a first internal volume 936 and a second internal volume 963. The inversion fold also divides the wall 909 into the outer layer 912 and an inner layer 938. The second internal volume 963 is inside an inner bell shape 911 (or mushroom shape) formed by the inner layer 938, and the first internal volume 936 is outside the inner bell shape 911, but inside the distal outer dome 916. The inner layer 938 has a contour that is similar to that of the outer layer 912 only at an inner band area 901 that is inside a waist portion 903 of the outer layer 912 that is between the proximal outer cover 914 and the distal outer dome 916. The inner layer 938 extends from the distal orifice 934 to the second end 910. The maximum outer diameter $d_{ob}$ of the inner bell shape 911 is less than the inner diameter $D_{IC}$ of the proximal outer cover 914, thus providing a third internal volume 905, which is substantially annular. The inner bell shape 911 extends proximally from the inversion fold 932. In some embodiments, the inner bell shape 911 has a maximum outer diameter $d_{ob}$ that is between about 30% and about 98% of an outer diameter Doc of the proximal outer cover 914. In some embodiments, the inner bell shape 911 has a maximum outer diameter $d_{ob}$ that is between about 50% and about 90% of the outer diameter Doc of the proximal outer cover 914. In some embodiments, the inner bell shape 911 has a maximum outer diameter $d_{ob}$ that is between about 60% and about 85% of the outer diameter Doc of the proximal outer cover 914.

In some embodiments, the outer diameter Doc of the proximal outer cover 914 is about the same as an outer diameter DOD of the distal outer dome 916. In some embodiments, the outer diameter Doc of the proximal outer cover 914 is smaller than the outer diameter DOD of the distal outer dome 916. In some embodiments, the outer diameter Doc of the proximal outer cover 914 is larger than the outer diameter DOD of the distal outer dome 916.

The outer waist 903 has an opposite inner face 907 that matches the contour of the inner bell shape 911 at the inner band area 901, although in other embodiments, a significant annular space may be present, and/or the contours may not match each other. The inner face 907 of the outer waist 903 has an inner face minimum diameter $D_{IFMIN}$ and an inner face maximum diameter $D_{IFMAX}$. In some embodiments, including the embodiment shown in FIG. 48, axial compression (e.g., from the aneurysm dome or from blood pressure) on the distal outer dome 916 of the occlusion device 900 if centered longitudinally can force a proximal face 913 of the inner bell shape 911 against an inner face 921 of the proximal outer cover 914, thus centering a force against the neck of the aneurysm. This is because the tapered contours of the inner face 907 and the inner band area 901 create annular space from each other as the inner bell shape 911 moves down in relation to the proximal outer cover 914. If instead, the axial compression from more of an outer portion of the aneurysm dome acts on the distal outer dome 916, the inner face 907 and the inner band area 901 can engage each other, for example, between a distal portion diameter $d_{dist}$ of the inner bell shape 911 and a proximal portion diameter (e.g., maximum outer diameter $d_{ob}$) of the inner bell shape 911, this transmitting the downward force onto both the inner bell shape 911 and the proximal face 915. The taper and other contours of the inner bell shape 911 and the waist area 903 can thus be modified, to control the amount of mechanical engagement between the outer layer 912 and the inner layer 938. The shape of the inner bell shape 911 (e.g., length vs. diameter or angle of taper, etc.) can be adjusted to control the amount of compressive resistance in the occlusion device 900 (e.g., resistance to compaction from blood pressure cycling). The proximal face 915 and the proximal face 913 create two layers adjacent the neck portion of the aneurysm. The dual layers at and adjacent the neck of the aneurysm serve to increase the overall density of the mesh (e.g., the total number of crossings, or the total pics per inch or pics per mm), to thus aid in the disruption or stagnation of flow at the neck.

A marker band 917 is attached over the two layers of wall 909 just distal to the ends 908, 910. The marker band 917 may comprise a radiopaque material such as platinum, platinum/iridium, or tantalum, for viewing on x-ray or fluoroscopy. The occlusion device 900 is fabricated as an inverted mesh tube 906 having a simple straight elongate configuration, and is subsequently formed into the shape shown in FIGS. 47-48 and heat set into this shape, to create an expanded state. For example, the occlusion device 900 may be constructed as a single layer mesh tube formed of at least some nickel-titanium alloy filaments, and then inverted on itself. The inverted mesh tube 906 may then be placed into a die or mold comprising one or more pieces, to hold it in the shape of the occlusion device 900. Then, the occlusion device 900 may be subjected to an elevated temperature and then cooled, to lock in the shape, resulting in an occlusion device 900 having at least some superelastic properties. The occlusion device 900 configured to be compressed or compacted within the lumen 654 of a delivery catheter 650 (e.g., microcatheter), having a distal end 652.

In the expanded state of the occlusion device 900, the inner bell shape 911 serves as an internal support to reduce the compressibility of the outer layer 812, and thus to maintain the shape of the entire expanded portion of the occlusion device 900, even through long-term implantation within an aneurysm. The inner bell shape 911, may comprise a larger density of crossings/pies (e.g., smaller average pore size) than the proximal outer cover 914 and/or the distal outer dome 916, to help increase distal stagnation or flow disruption nidus. The inner bell shape 911 may have a significantly smaller pore size than the proximal outer cover 914 and/or the distal outer dome 916 when the occlusion device 900 is in its expanded state. Thus, the occlusion device 900 may include a distal stagnation zone (inner bell shape 911 and distal outer dome 916) and a proximal stagnation zone (inner bell shape 911 and proximal outer cover 914).

The occlusion device 900 is detachably coupled at a detachable joint 940 at its proximal end 902 to a pusher wire 942 having a distal end 944 and a proximal end 946. The detachable joint 940 may comprise one of a number of detachment systems, including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems. In any of the embodiments disclosed herein, alternative detachable joint may be employed, such as the detachable joints disclosed in U.S. Pat. No. 11,058,431, issued Jul. 13, 2021, and entitled "Systems and Methods for Treating Aneurysms" and in U.S. Pat. No. 10,856,880, issued Dec. 8, 2020, and entitled "Systems and Methods for Treating Aneurysms."

Figure 56:
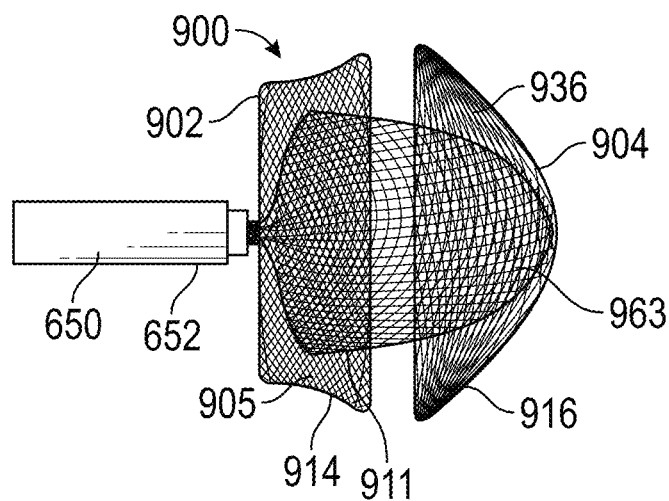

FIGS. 49-56 illustrate the delivery of the occlusion device 900 from its compressed state within the lumen 654 of a delivery catheter 650 to its expanded state. FIG. 49 illustrates the distal end 652 of the delivery catheter 650. FIG. 50 illustrates the initial delivery of the occlusion device 900 out of the lumen 654 of the delivery catheter 650 by pushing the pusher wire 942 at its proximal end 946. The majority of the occlusion device 900 is still significantly compressed. As the pusher wire 942 is further pushed distally, the occlusion device 900 begins to further exit the lumen 654 and expand, as shown in FIG. 51. The inner bell shape 911, the distal outer dome 916, and the proximal outer cover 914 can be seen expanding in FIGS. 52-55, respectively. In FIG. 56, the inner bell shape 911, the distal outer dome 916, and the proximal outer cover 914 each take their expanded shapes of the occlusion device 900 in its expanded state, without any of the restraints of the lumen 654 of the delivery catheter 650. An occlusion device 900 having a 3 mm to 6 mm expanded outer diameter may fit within the inner lumen of a microcatheter having a 0.023 inch inner diameter, or a 0.021 inch inner diameter, or even a 0.017 inch inner diameter.

Figure 57:
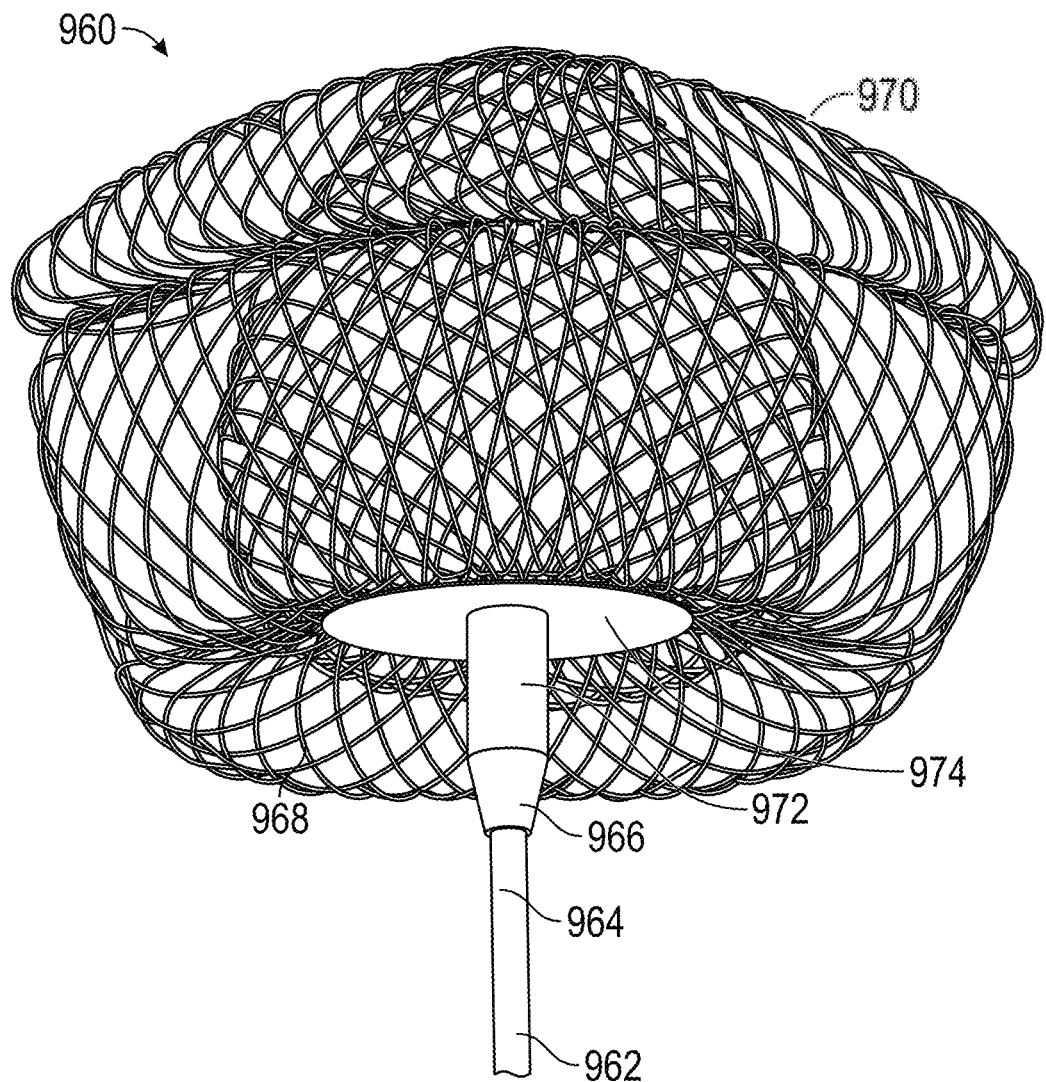
FIG. 57 is a perspective view of an occlusion device, according to an embodiment of the present disclosure.

FIG. 57 illustrates an embodiment of a mesh occlusion device 960 having features that may be utilized in any of the other occlusion devices 200, 300, 400, 500, 600, 700, 800, 900 disclosed herein. The occlusion device 960 has a proximal end 968 and a distal end 970 and is attached to a distal end 964 of a pusher wire 962 via a marker band 972 and a detachable joint 966, as previously described herein in relation to the other embodiments. A central circle of the proximal end 968 comprises a polymeric seal 974 that fills the adheres to and/or covers the individual wires or filaments comprising the mesh (e.g., inverted mesh tube). In some embodiments, the polymer seal 974 comprises polyurethane. In some embodiments, the polymer seal 974 comprises other thermoplastic elastomers, or comprises non-thermoplastic elastomers. In some embodiments, the polymer seal 974 comprises PTFE, PETE, or other fluoropolymers. In some embodiments, the polymer seal 974 comprises a bioabsorbable polymer. Though the diameter of the polymer seal 974 shown in FIG. 57 is less than the maximum diameter of the proximal end 968 of the occlusion device 960, in other embodiments, the diameter of the polymer seal 974 may include substantially the entire diameter of the proximal end 968, and may in some embodiments, even continue onto a portion of the outer diameter (e.g., lateral cylindrical wall) of the device 960. The thickness of the polymer seal 974 (e.g., coating thickness) may range between about 5 microns to about 2,000 microns. The polymer seal 974 serves to significantly stop flow through at least a portion of the proximal end 968 of the occlusion device 960, further stagnating blood flow into the aneurysm when the occlusion device 960 is implanted.

While the foregoing is directed to embodiments of the present disclosure, other and further embodiments may be devised without departing from the basic scope thereof. The filament diameter of the filaments comprising any of the mesh material (e.g., mesh tube including inverted mesh tubes) described herein may be between about 0.0004 inch and about 0.003 inch, or between about 0.0005 inch and about 0.002 inch, or between about 0.0006 inch and about 0.002 inch, or between about 0.0006 inch and about 0.0015 inch. The drawn filled tubes (DFT) may comprise between 0% and 100% of the total strands/filaments in any of the braided/mesh tubes. In some embodiments, the drawn filled tubes (DFT) comprise about 50% to about 100% of the total filaments of the cover and about 50% to about 100% of the total filaments of each of the doubled-over or looped tubular mesh. The radiopaque core of each of at least some of the drawn filled tubes has a cross-sectional area that is between about 10% and about 70% of the total cross-sectional area of the each of at least some of the drawn filled tubes, or between about 51% and about 70% of the total cross-sectional area of the each of at least some of the drawn filled tubes. In some embodiments, NiTi #1-DFT® wire produced by Fort Wayne Metals Research Products Corp. (Fort Wayne, IN USA) may be utilized. The filaments may be braided with patterns having filament crossings that are in any one or more of the following ratios of filaments: 1×1, 1×2, 2×1, 2×2, 2×3, 3×2, 3×3, etc. (e.g., warp and weft). Any low, moderate, or high pick counts may be used, for example, between about 15 picks per inch and about 300 picks per inch, or between about 20 picks per inch and about 160 picks per inch. Any of the filaments or any of the portion of the occlusion devices may be coated with compounds that enhance endothelialization, thus improving the healing process when implanted within the aneurysm, and optimizing occlusion. The pusher and occlusion device configurations presented herein may also be used for in other types of implantable devices, such as stents, flow diversion devices, filters, and occlusion devices for structural heart defects.

Additional materials may be carried on the cover of the occlusion device, or any other proximal portion of the occlusion device, and configured to face opposite the aneurysm neck. In some embodiments, the material on the occlusion device may comprise a biological layer, configured to encourage growth. In some embodiments, the biological layer may comprise antibodies, in order to accelerate the formation of an endothelial layer, for example, by attracting endothelial progenitor cells (EPCs). In some embodiments, the biological layer may comprise a natural membrane or structure, such as a membrane, such as a membrane from an ear, or a cornea, or an ultra-thin piece of ligament, or even a piece of blood vessel wall. In some embodiments, the material on the occlusion device may comprise a polymer layer configured to act as a simulated arterial wall. In some embodiments, the polymer layer may comprise polytetrafluoroethylene, such as expanded polytetrafluoroethylene (ePTFE), such as that used in grafts. Occlusion devices as described herein may incorporate biological or polymeric layers, such as those described in co-pending U.S. Pat. No. 11,202,636, issued Dec. 21, 2021, and entitled "Systems and Methods for Treating Aneurysms," which is hereby incorporated by reference in its entirety for all purposes.

The delivery catheter may be a microcatheter having a luminal diameter of 0.017 inch or 0.021 inch, 0.025 inch, or 0.028 inch, or other sizes. An elongate pusher may comprise a wire, a hypo tube, or another elongate structure having column support, and is detachably coupled at its distal end to the proximal end of the occlusion device. A detachable joint may comprise one of a number of detachment systems, including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems.

In any of the braided embodiments, braided elements can be subsequently etched (chemical etch, photochemical etch) to decrease the overall wire diameter and decrease the stiffness.

Though multiple embodiments have been presented, other embodiments are possible using the teachings herein by combining any of the features. For example, a device having the curvilinear contours 264, 364 along the distal surface 260 may also be constructed having any of the shapes of the inner layer of the two-layer braid, such as those shown in the embodiments of FIG. 1, 12A, 19, 20, 29, 31, 38, 47, or 57 (or occlusion devices 300, 400, 500, 600, 700, 800, 900, 960). Furthermore, a device having the curvilinear contours 264, 364 along the distal surface 260 may also be constructed having any of the shapes of the outer layer of the two-layer braid, such as those shown in the embodiments of FIG. 1, 12A, 19, 20, 29, 31, 38, 47, or 57 (or occlusion devices 300, 400, 500, 600, 700, 800, 900, 960). Or, as another example, a ball 611 and a distal column 753 may be formed longitudinally adjacent each other on an inner layer. In some embodiments, the ball 611 may be proximal to the distal column, but in other embodiments a ball may actually be placed distal to a column. In case wherein any features may appear to be uncombinable, based on the particular embodiments presented herein, they may nevertheless be combinable by simply changing one or more dimensions, to allow them to fit or morph together.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

For purposes of the present disclosure and appended claims, the conjunction "or" is to be construed inclusively (e.g., "an apple or an orange" would be interpreted as "an apple, or an orange, or both"; e.g., "an apple, an orange, or an avocado" would be interpreted as "an apple, or an orange, or an avocado, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure and appended claims, the words "comprising," "including," "having," and variants thereof, wherever they appear, shall be construed as open-ended terminology, with the same meaning as if the phrase "at least" were appended after each instance thereof.

What is claimed is:

1. An apparatus for treating an aneurysm in a blood vessel, comprising:
   an occlusion element configured to be releasably coupled to an elongate delivery shaft and configured to be delivered in a collapsed configuration through an inner lumen of a delivery catheter, the occlusion element comprising an inverted mesh tube having a first end, a second end, an outer layer, and an inner layer, the outer layer transitioning to the inner layer at a distal inversion portion, the first end and the second end located at a proximal end of the occlusion element,
   wherein the outer layer comprises a distal dome, a proximal cover having a proximal outer face configured to cover an aneurysmal neck, and a reduced-diameter waist between the distal dome and the proximal cover, the reduced-diameter waist having an inner face, the inner face having a minimum diameter and a maximum diameter, wherein the inner layer comprises a distal portion having a distal portion diameter that is less than the minimum diameter of the inner face, and wherein the inner layer further comprises a proximal portion having a proximal portion diameter that is greater than the maximum diameter of the inner face, such that the inner face is configured to engage an intermediate portion of the inner layer when sufficient downward axial compression is applied on the distal dome in relation to the proximal outer face.

2. The apparatus of claim 1, wherein the inner layer comprises a bell shape.

3. The apparatus of claim 2, wherein the inner face is configured to match a first contour of the bell shape.

4. The apparatus of claim 3, wherein the inner face comprises a tapered surface.

5. The apparatus of claim 1, wherein the inner layer comprises a tapered diameter decreasing between the proximal portion diameter and the distal portion diameter.

6. The apparatus of claim 5, wherein the inner face is configured to match a portion of the tapered diameter.

7. The apparatus of claim 6, wherein the inner face comprises a tapered surface.

8. The apparatus of claim 1, wherein the inverted mesh tube has a first density of crossings at the inner layer and a second density of crossings at the proximal cover, the first density of crossings larger than the second density of crossings.

9. The apparatus of claim 1, further comprising a polymeric seal carried on a portion of the proximal outer face.

10. The apparatus of claim 9, wherein the polymeric seal comprises a bioabsorbable polymer.

11. An apparatus for treating an aneurysm in a blood vessel, comprising:

an occlusion element configured to be releasably coupled to an elongate delivery shaft and configured to be delivered in a collapsed configuration through an inner lumen of a delivery catheter, the occlusion element comprising an inverted mesh tube having a first end, a second end, an outer layer, and an inner layer, the outer layer transitioning to the inner layer at a distal inversion portion, the first end and the second end located at a proximal end of the occlusion element, wherein the outer layer comprises a distal dome, a proximal cover configured to cover an aneurysmal neck, and a reduced-diameter waist between the distal dome and the proximal cover, the reduced-diameter waist having an inner face, the inner face having a minimum diameter, a maximum diameter, and a tapered surface extending between the minimum diameter and the maximum diameter, wherein the inner layer comprises a distal portion having a distal portion diameter that is less than the minimum diameter of the inner face, and wherein the inner layer further comprises a proximal portion having a proximal portion diameter that is greater than the maximum diameter of the inner face, and wherein a portion of the inner layer, between the distal portion and the proximal portion is configured to be engageable with the inner face.

12. The apparatus of claim 11, wherein the inner layer comprises a bell shape.

13. The apparatus of claim 11, wherein the inner layer comprises a tapered diameter decreasing between the proximal portion diameter and the distal portion diameter.

14. The apparatus of claim 11, wherein the inverted mesh tube has a first density of crossings at the inner layer and a second density of crossings at the proximal cover, the first density of crossings larger than the second density of crossings.

15. The apparatus of claim 11, further comprising a polymeric seal carried on a proximal portion of the proximal cover.

16. The apparatus of claim 15, wherein the polymeric seal comprises a bioabsorbable polymer.

17. The apparatus of claim 11, wherein the inner face is configured to engage the portion of the inner layer when sufficient downward axial compression is applied on the distal dome in relation to the proximal cover.

18. The apparatus of claim 11, wherein the inner layer comprises a proximal outer face and wherein the proximal cover has a proximal inner face, and wherein the proximal outer face of the inner layer is configured to be forced against the proximal inner face of the proximal cover when sufficient axial compression is centrally applied on the distal dome, in relation to the proximal cover.

19. The apparatus of claim 11, wherein the proximal cover has a proximal cover outer diameter and the distal dome has a distal dome outer diameter, the proximal cover outer diameter about the same as the distal dome outer diameter.

20. The apparatus of claim 11, wherein the proximal cover has a proximal cover outer diameter and the inner layer has an inner layer maximum outer diameter, the inner layer maximum outer diameter between about 30% and about 98% of the proximal cover outer diameter.

* * * * *